US006146829A

United States Patent [19]
Cook et al.

[11] Patent Number: 6,146,829
[45] Date of Patent: Nov. 14, 2000

[54] GAPPED 2' MODIFIED OLIGONUCLEOTIDES

[75] Inventors: Phillip Dan Cook, Vista; Brett P. Monia, Carlsbad, both of Calif.

[73] Assignee: Isis Pharmaceuticals, Inc., Carlsbad, Calif.

[21] Appl. No.: 09/144,611

[22] Filed: Aug. 31, 1998

Related U.S. Application Data

[62] Division of application No. 08/861,306, Apr. 21, 1997, Pat. No. 5,856,455, which is a division of application No. 08/244,993, filed as application No. PCT/US92/11339, Dec. 23, 1992, Pat. No. 5,623,065, which is a continuation-in-part of application No. 08/007,996, Jan. 21, 1993, abandoned, which is a continuation-in-part of application No. 07/814,961, Dec. 24, 1991, abandoned.

[51] Int. Cl.$^7$ .................................................. C12Q 1/68
[52] U.S. Cl. ............................................................. 435/6
[58] Field of Search ........................... 435/6, 91.5, 91.51, 435/91.53, 199; 536/23.1, 24.3, 24.5

[56] References Cited

U.S. PATENT DOCUMENTS

| | | | |
|---|---|---|---|
| 4,867,187 | 9/1989 | Duck | 435/6 |
| 4,908,307 | 3/1990 | Rodland et al. | 435/6 |
| 5,013,830 | 5/1991 | Ohtsuka et al. | 536/25.1 |
| 5,034,506 | 7/1991 | Summerton et al. | 528/391 |
| 5,134,066 | 7/1992 | Rogers et al. | 435/91.3 |
| 5,149,797 | 9/1992 | Pederson et al. | 536/23.1 |
| 5,220,007 | 6/1993 | Pederson et al. | 536/23.1 |
| 5,256,775 | 10/1993 | Froehler | 536/25.6 |
| 5,366,878 | 11/1994 | Pederson et al. | 435/91.3 |
| 5,403,711 | 4/1995 | Walder et al. | 435/6 |
| 5,466,786 | 11/1995 | Buhr et al. | 536/26.26 |
| 5,623,065 | 4/1997 | Cook et al. | 536/23.1 |
| 5,652,355 | 7/1997 | Metelev et al. | 536/24.5 |
| 5,658,731 | 8/1997 | Sproat et al. | 435/6 |
| 5,856,455 | 1/1999 | Cook | 536/23.1 |
| 5,955,589 | 9/1999 | Cook et al. | 536/23.1 |
| 5,962,425 | 10/1999 | Walder et al. | 514/44 |

FOREIGN PATENT DOCUMENTS

| | | |
|---|---|---|
| 2017369 | 11/1990 | Canada . |
| 0 260 032 | 8/1987 | European Pat. Off. . |
| 365627B1 | 3/1989 | European Pat. Off. . |
| 0 339 842 | 4/1989 | European Pat. Off. . |
| 0 339 330 | 11/1990 | European Pat. Off. . |
| 39 15 462 | 9/1990 | Germany . |
| 41 10 085 | 10/1992 | Germany . |
| 3-240795 | 10/1991 | Japan . |
| WO 89/05358 | 6/1989 | WIPO . |
| WO 90/15814 | 6/1990 | WIPO . |
| WO 91/06556 | 10/1990 | WIPO . |
| WO 91/15499 | 4/1991 | WIPO . |
| WO 91/12323 | 8/1991 | WIPO . |
| WO 94/02498 | 2/1994 | WIPO . |
| WO 92/07065 | 9/1994 | WIPO . |

OTHER PUBLICATIONS

Inoue et al. (1987). Sequence–dependent hydrolysis of RNA using modified oligonucleotide splints and RNase H. FEBS Lett. 215(2): 327–330.

Agrawal, S. et al., "Oligodeoxynucleoside Phosphoramidates and Phosphorothioates as Inhibitors of Human Immunodeficiency Virus", *Proc. Natl. Acad. Sci. USA*, 1988, 85, 7079–7083.

Augustyns et al., "Influence of the Incorporation of (S)–9–(3,4–dihydroxy–butyl) Adenine on the Enzymatic Stability and Base–Pairing Properties of Oligodeoxynucleotides", *Nucl. Acids Res.*, 1991, 19, 2587–2593.

Beaton et. al., Chapter 5, Synthesis of oligonucleotide phosphorodithioates, p. 109, *Oligonucleotides and Analogs, A Practical Approach*, Eckstein, F. (Ed.), IRL Press, New York, 1991, pp. 109–135.

Borthwick et al., "Synthesis of Chiral Carbocylic Nucleosides", *Tetrahedron*, 1992, 48, 571–623.

Brill et al.,"Synthesis of Deoxydinucleoside Phosphorodithioates", *J. Am. Chem. Soc.*, 1991, 113, 3972–3980.

Cohen in *Oligonucleotides: Antisense Inhibitors of Gene Expression*, CRC Press, Inc., Boca Raton, FL (1989), p. 1–255.

Dagle et al., "Physical properties of oligonucleotides containing phosphoramidate–modified internucleoside linkages", *Nucl. Acids Res.*, 1991, 19, 1805–1810.

Dagle et al., "Targeted degradation of mRNA in Xenopus oocytes and embryos directed by modified oligonucleotides: studies of An2 and cyclin in embryogenesis", *Nucl. Acids Res.*, 1990, 18, 4751–4757.

Dagle et al., "Pathways of Degradation and Mechanism of Action of Antisense Oligonucleotides in *Xenopus laevis* Embryos", *Antisense Research and Development*, 1991, 1, 11–20.

Debart et al., "Intermolecular Radical C—C Bond Formation: Synthesis of a Novel Dinucleoside Linker for Non–anionic Antisense Oligonucleotides", *Tetra. Lett.*, 1992, 33, 2645–2648.

Eder, P.S. and Walder, J.A., "Ribonuclease H from K562 Human Erythroleukemia Cells", *J. Biol. Chem.*, 1991, 266(10), 6472–6479.

Gagnor et. al., "α–DNA VIA: Comparative Study of α– and β–Anomeric Oligodeoxyribonucleotides in Hybridization to mRNA and in Cell Free Translation Inhibition", *Nucl. Acids Res.*, 1987, 15, 10419–10436.

Gait et al., "Synthetic Analogues of Polynucleotides. Part XII. Synthesis of Thymidine Derivatives Containing an Oxyacetamido– or and Oxyformamido–Linkage Instead of a Phosphodiester Group", *J.C.S Perkins I*, 1974, 1684–1686.

(List continued on next page.)

*Primary Examiner*—Robert A. Schwartzman
*Assistant Examiner*—Thomas G. Larson
*Attorney, Agent, or Firm*—Woodcock Washburn Kurtz Mackiewicz & Norris LLP

[57] ABSTRACT

Oligonucleotides and other macromolecules are provided that have increased nuclease resistance, substituent groups for increasing binding affinity to complementary strand, and sub-sequences of 2'-deoxy-erythro-pentofuranosyl nucleotides that activate RNase H enzyme. Such oligonucleotides and macromolecules are useful for diagnostics and other research purposes, for modulating protein in organisms, and for the diagnosis, detection and treatment of other conditions susceptible to antisense therapeutics.

15 Claims, 2 Drawing Sheets

OTHER PUBLICATIONS

Greenberg, M.E. in Current Protocols in Molecular Biology, Ausubel et al. (Eds.), John Wiley and Sons, NY (1994).

Kawasaki et al., Synthesis and Biophysical Studies of 2'–dRIBO–2'–F Modified Oligonucleotides, Conference On Nucleic Acid Therapeutics, Clearwater, FL, Jan. 13, 1991.

Kawasaki et al., "Uniformly Modified 2'–Deoxy–2'–fluoro Phosphorothioate Oligonucleotides as Nuclease–Resistant Antisense Compounds with High Affinity and Specificity for RNA Targets", J. Med. Chem., 1993, 36, 831–841.

Kierzek et. al., "Association of 2'–5' Oligoribonucleotides", Nucl. Acids Res., 1992, 20, 1685–1690.

Kirshenbaum et. al., The 5th San Diego Conference: Nucleic Acids: New Frontiers, Poster abstract 28, Nov. 14–16, 1990.

Matteucci et al., "Deoxyoligonucleotides Bearing Neutral Analogues of Phosphodiester Linkages Recognize Duplex DNA via Triple–Helix Formation", J. Am. Chem. Soc., 1991, 113, 7767–7768.

Matteucci, "Hybridization Properties of a Deoxyoligonucleotide Containing Four Formacetal Linkages", Nucleosides & Nucleotides, 1991, 10, 231–234.

Matteucci, "Deoxyoligonucleotide Analogs Based on Formacetal Linkages", Tetrahedron Letters, 1990, 31 2385–2388.

Mertes and Coats, "Synthesis of Carbonate Analogs of Dinucleotides. 3'–Thymidinyl 5–40 –Thymidinyl Carbonate, 3'–Thymidinyl 5'–(5–Fluoro–2'–deoxyuridinyl) Carbonate, and 3'–(5–Fluoro–2'–deoxyuridinyl) 5'–Thymidinyl Carbonate", J. Med. Chem., 1969, 12, 154–157.

Miller et al., "Effects of a Trinucleotide Ethyl Phosphotriester, $G^mp(Et)G^mp(Et)U$, on Mammalian Cells in Culture", Biochemistry, 1977, 16, 1988–1996.

Miller et. al., Chapter 6, Synthesis of oligo–2'–deoxyribonucleoside methyl–phosphonates, p. 137, Oligonucleotides and Analogs, A Practical Approach, Eckstein, F., Ed.; The Practical Approach Series, IRL Press, New York, 1991.

Miller and Ts'o, "A New Approach to Chemotherapy Based on Molecular Biology and Nucleic Acid Chemistry: Matagen (Masking Tape for Gene Expression)", Anti–Cancer Drug Design, 1987, 2, 117–128.

Miller et al., "Oligonucleotide Inhibitors of Gene Expression in Living Cells: New Opportunities in Drug Design", Annual Reports in Medicinal Chemistry, 1988, Ch. 30, 295–304.

Monia et al., "Evaluation of 2'–Modified Oligonucleotides Containing 2'–Deoxy Gaps as Antisense Inhibitors of Gene Expression", J. Bio. Chem., 1993, 208, 14514–14522.

Musicki and Widlanski, "Synthesis of Nucleoside Sulfonates and Sulfones", Tetrahedron Letters, 1991, 32, 1267–1270.

Musicki and Widlanski, "Synthesis of Carbohydrate Sulfonates and Sulfonate Esters", J. of Organic Chemistry, 1990, 55, 4231–4233.

Cormier and Ogilvie, "Synthesis of Hexanucleotide Analogues Containing Diisopropylsilyl Internucleotide Linkages", Nucl. Acids Res., 1988, 16, 4583–4594.

Ogilvie and Cormier, "Synthesis of a Thymidine Dinucleotide Analogue Containing an Internucleotide Silyl Linkage", Tetra. Lett., 1985, 26, 4159–4162.

Perbost et al., "Sugar Modified Oligonucleotides I. Carbo–Oligodeoxynucleotides as Potential Antisense Agents", Biochem. Biophys. Res. Commun., 1989, 165, 742–747.

Petersen et al., "Chemical Synthesis of Dimer Ribonucleotides Containing Internucleotidic Phosphoradithioate Linkages", Tetra. Lett., 1990, 31, 911–914.

Sagi et al., "Biochemical Properties of Oligo[(+)–Carbocyclic–Thymidylates] and Their Complexes", Nucl. Acids Res., 1990, 18, 2133–2140.

Saison–Behmoaras et al., "Short Modified Antisense Oligonucleotides Directed against Ha–ras Point Mutation Induce Selective Cleavage of the mRNA and Inhibit T24 Cells Proliferation", EMBO J., 1991, 10, 1111–1118.

Schneider et al., "Oligonucleotides Containing Flexible Nucleoside Analogues", J. Am. Chem. Soc., 1990, 112, 453–455.

Schneider, K. Christian and Benner, Steven A., "Building Blocks for Oligonucleotide Analogs with Dimethylene–Sulfide, Sulfoxide, and Sulfone Groups Replacing Phosphodiester Linkages" Tetra Lett., 1990, 31, 335–338.

Secrist, et. al., "Synthesis and Biological Activity of 4'–Thionucleosides" Tenth International Roundtable: Nucleosides, Nucleotides and Their Biological Evaluation, Sep. 16–20, 1992, Abstracts of Papers, Abstract 21.

Stawinski Jacek and Thelin Mats, Tenth International Roundtable: Nucleosides, Nucleotides and Their Biological Evaluation, Sep. 78, 1992, Abstracts of Papers, Abstract 80.

Szemzo et. al., "First Synthesis of Carbocyclic Oligothymidylates", Tetra. Lett., 1990, 31, 1463–1466.

Vasseur et al., "Oligonucleosides: Synthesis of Novel Methylhydroxylamine–Linked Nucleoside Dimer and Its Incorporation into Antisense Sequences", J. Am. Chem. Soc., 1992 114, 4006–4007.

Veeneman et al., "Synthesis of Oligodeoxynucleotides Containing Thymidines Linked Via an Internucleosidic–(3'–5')–Methylene Bond", Recueil des Travaux Chimiques des Pays–Bas, 1990 109, 7–8, 449–451.

Berkowitz et al., "Synthesis of 1,2–Dihydro–1–(2deoxy–β–D–Erythropentafuranosyl)–2–Oxopyrazine 4–oxide", J. Med. Chem., 1973, 16(2), 183–184.

Inoue et al., "Sequence–dependent Hydrolysis of RNA Using Modified Oligonucleotide Splints and R Nase H", Febs. Ltrs., 1987, 215, 327–330.

Inoue et al., "Synthesis and Hybridization Studies on Two Complementary Nona(2'–O–Methyl)Ribonucleotides", Nucl. Acids. Res., 1987, 15, 6131–6148.

Inoue et al., "Synthesis and Properties of Novel Nucleic Acid Probes", Nucl. Acids Res., Symposium Series, 1985, 16, 165–168.

Agris et al., "Inhibition of Vesicular Stomatitis Virus Protein Synthesis and Infection by Sequence–Specific Oligodeoxyribonucleoside Methylphosphonates", Biochem., 1986, 25(20), 6268–6275.

Atkinson and Smith, "Solid–Phase Synthesis of Oligodeoxyribonucleotides by the Phosphite–triester Method", Oligonucleotide Synthesis a practical approach, Ch. 3, 35–81, 1991.

Biggadike et al., "Short Convergent Route to Homochiral Carbocyclic 2'–Deoxynucleosides and Carbocyclic Ribonucleosides", J. Chem. Soc., Chem Commun., 1987, 1083–1084.

Brill et al., "Synthesis of Oligodeoxynucleoside Phosphorodithioates via Thioamidites", J. Am. Chem. Soc., 1989, 111, 2321–2322.

Castle and Seese, "Imidazo[4,5–d]pyridazines I. Synthesis of 4,7–Disubstituted Derivatives", J. Org. Chem., 1958, 23, 1534–1538.

Cazenave et al., "Enzymatic Amplification of Translation Inhibition of Rabbit β–globin mRNA Mediated by Anti–Messenger Oligodeoxynucleotides Covalently Linked to Intercalating Agents", *Nucleic Acids Research*, 1987, 15(12), 4717–4736.

Constant et al., "Hetereodimeric Molecules Including Nucleic Acid Bases and 9–Aminoacridine. Spectroscopic Studies, Conformations, and Interactions with DNA", *Biochemistry*, 1988, 27, 3997–4003.

Dreyer and Dervan, "Sequence–Specific Cleavage of Single–Stranded DNA: Oligodeoxynucleotide–EDTA–Fe(II)", *Proc. Natl. Acad. Sci. USA*, 1985, 82, 968–972.

Freskos, J.N., "Synthesis of 2'–Deoxypyrimidine Nucleosides Via Copper (I) Iodide Catalysis", *Nucleosides & Nucleotides*, 1989, 8(5&6), 1075–1076.

Jarvi et al., "Synthesis and Biological Evaluation of Dideoxunucleosides Containing a Difluorokethylene Unit", *Nucleosides & Nucleotides*, 1989, 8(5&6), 1111–1114.

Jayaraman et al., "Selective Inhibition of *Escherichia Coli* Protein Synthesis and Growth by Nonionic Oligonucleotides Complementary to the 3' End of 16S rRNA", *Proc. Natl. Acad. Sci. USA*, 1981, 78(3), 1537–1541.

Jones, R.A., "Preparation of Protected Deoxyribonucleosides", from *Oligonucleotide Synthesis–A Practical Approach*, 1991, Ch. 2, 23–34.

Jones et al., "4–Substituted Nucleosides. 5. Hydroxymethylation of Nucleoside 5'–Aldehydes", *J. Org. Chem.*, 1979, 44(8), 1309–1317.

Kazimierczuk et al., "Synthesis of 2'–Deoxytubercidin, 2'–Deoxyadenosine, and Related 2'–deoxynucleosides via A Novel Direct Stereospecific Sodium Salt Glycosylation Procedure", *J. Am. Chem. Soc.*, 1984, 106, 6379–6382.

Le Doan et al., "Sequence–Targeted Chemical Modifications of Nucleic Acids by Complimentary Oligonucleotides Covalently Linked to Porphyrins", *Nucl. Acids Res.*, 1987, 15(21), 8643–8659.

Letsinger et al., "Effects of Pendant Groups at Phosphorus on Binding Properties of d–ApA Analogues", *Nucleic Acids Research*, 1986, 14(8), 3487–3499.

Matsukura et al., "Phosphorothioate Analogs of Oligodeoxynucleotides: Inhibitors of Replication and Cytopathic Effects of Human Immunodeficiency Virus", *Proc. Natl. Acad. Sci. USA*, 1987, 84, 7706–7710.

Meyer et al., "Efficient, Specific Cross–Linking and Cleavage of DNA by Stable, Synthetic Complementary Oligodeoxynucleotides", *J. Am. Chem. Soc.*, 1989, 111, 8517–8519.

Miller et al., "Biochemical and Biological of Nonionic Nucleic Acid Methylphosphonates", *Biochemistry*, 1981, 20 1874–1880.

Miller et al., "Nonionic Nucleic Acid Analogues. Synthesis and Characterization of Dideoxyribonucleoside Methylphosphonates", *Biochemistry*, 1979, 18, 5134–5142.

Miller et al., "Synthesis and Properties of Adenine and Thymine Nucleoside Alkyl Phosphotriesters, the Neutral Analogs of Dinucleoside Monophosphates", *J. Am. Chem. Soc.*, 1971, 93(24), 6657–6664.

Outten, R.A., "Synthetic 1–Methoxybenzo[d]naphtho[1,2–b]pyran–6–one C–Glycosides", *J. Org. Chem.*, 1987, 52(22), 5064–5066.

Revankar et al., "Synthesis and Antiviral/Antitumor Activities of Certain 3–Deazaguanine Nucleosidea and Nucleotides", *J. Med. Chem.*, 1984, 27, 1389–1396.

Robins et al., "Nucleic–Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.*, 1983, 105, 4059–4065.

Roelen et al., "Synthesis of Nucleic Acid Methylphosphonthioates", *Nucleic Acids Research*, 1988, 16(15), 7633–7645.

Ruby and Abelson, "An Early Hierarchic Role of U1 Small Nuclear Ribonucleoprotein in Spliceosome Assembly", *Science*, 1988, 242, 1028–1035.

Sigman, D.S., "Nuclease Activity of 1,10–Phenanthroline–Copper Ion", *Acc. Chem. Res.*, 1986, 19, 180–186.

Smith et al., "Antiviral Effect of an Oligo(nucleoside Methylphosphonate) Complementary to the Splice Junction of Herpes Simplex Virus Type 1 Immediate Early pre–mRNAs 4 and 5", *Proc. Natl. Acad. Sci. USA*, 1986, 83, 2787–2791.

Stein, C.A., "Physiochemical Properties of Phosphorothioate Oligodeoxynucleotides", *Nucleic Acids Research*, 1988, 16(8), 3209–3221.

Suciu and Lerner, "Synthesis of 9–(2,5–dideoxy–β–D–glycero–pent–4–enofuranosyl)adenine", *Carbohydrate Research*, 1975, 44, 112–115.

Tidd et al., "Evaluation of N–ras Oncogene Anti–Sense, Sense and Nonsense Sequence Methylphosphonate Oligonucleotide Analogues", *Anti–Cancer Drug Design*, 1988, 3, 117–127.

van der Krol, "Modulation of Eukaryotic Gene Expression by Complementary RNA or DNA Sequences", *BioTechniques*, 1988, 6(10), 958–974.

Walder and Walder, "Role of RNase H in Hybrid–Arrested Translation by Antisense Oligonucleotides", *Proc. Natl. Acad. Sci. USA*, 1988, 85, 5011–5015.

Yeung et al., "Photoreactivities and Thermal Properties of Psoralen Cross–Links", *Biochemistry*, 1988, 27, 3204–3210.

Zon, G., "Synthesis of Backbone–Modified DNA Analogues for Biological Applications", *J. Protein Chem.*, 1987, 6(2), 131–145.

Block et al., *Gene*, 1988, 72, 349–360.

Uhlmann et al., "Antisense oligonucleotides: A new therapeutic principle", *Chem. Reviews*, 1990, 90(4), 544–584.

Ikehara et al., *Nucl. Acids Res.*, 1977, 4(12), 4249–4260.

Antisense '97: A roundtable on the state of the industry, *Nature Biotech.*, 1997, 15, 519–524.

Fujimori et al., "Enantio–DNA recognizes complementary RNA but not complementary DNA", *J. Am. Chem. Soc.*, 1990, 112(20), 7436–7438.

Gewirtz et al., "Facilitating oligonucleotide delivery: Helping antisense deliver on its promise", *Proc. Natl. Acad. Sci. USA*, 1996, 93, 3161–3163.

Gura, "Antisense has growing pains", *Science*, 1995, 270, 575–577.

Milligan et al., "Current concepts in antisense drug design", *J. Med. Chem.*, 1993, 36(14), 1923–1937.

Stull et al., "Antigene, ribozyme and aptamer nucleic acid drugs: Progress and prospects", *Pharm. Res.*, 1995, 12(4), 465–483.

SEQUENCE LISTING

<160> NUMBER OF SEQ ID NOS: 12

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
ccacaccgac ggcgccc                                                   17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2
ccacaccgac ggcgccc                                                   17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
ccacaccgac ggcgccc                                                   17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
ccacaccgac ggcgccc                                                   17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
ccacaccgac ggcgccc                                                   17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6
ccacaccgac ggcgccc                                                    17

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
acattatgct agcttttga gtaaacttgt ggggcaggag accctgt              47

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
gagatctgaa gcttctggat ggtcagcgc                                 29

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
gagatctgaa gcttgaagac gccaaaaaca taaag                          35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
acgcatctgg cgcgccgata ccgtcgacct cga                            33

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11 gcgtttttt tttgcg                                                16

<210> SEQ ID NO 12
<211> LENGTH: 19
<212> TYPE: DNA
<213> ORGANISM: Artificial Sequence
<220> FEATURE:

```
<223> OTHER INFORMATION: Description of Artificial Sequence:  Novel
      Sequence

<400> SEQUENCE: 12
cgcaaaaaaa aaaaaacgc                                                    19
```

GAPPED 2' MODIFIED OLIGONUCLEOTIDES

This application is a division of application Ser. No. 08/861,306, filed on Apr. 21, 1997 (now U.S. Pat. No. 5,856,455), which is a division of application Ser. No. 08/244,993, filed on Jun. 21, 1994 (now U.S. Pat. No. 5,623,065), which was filed as international patent application PCT/US92/11339, on filed Dec. 23, 1992. Application Ser. No. 08/244,993 also is a continuation-in-part of application Ser. No. 07/814,961, filed on Dec. 24, 1991, now abandoned, and of application Ser. No. 08/007,996, filed on Jan. 21, 1993, now abandoned.

FIELD OF THE INVENTION

This invention is directed to the synthesis and use of oligonucleotides and macromolecules to elicit RNase H for strand cleavage in an opposing strand. Included in the invention are oligonucleotides wherein at least some of the nucleotides of the oligonucleotides are functionalized to be nuclease resistant, at least some of the nucleotides of the oligonucleotide include a substituent that potentiates hybridization of the oligonucleotide to a complementary strand, and at least some of the nucleotides of the oligonucleotide include 2'-deoxy-erythro-pentofuranosyl sugar moieties. The oligonucleotides and macromolecules are useful for therapeutic peutics, diagnostics and as research reagents.

BACKGROUND OF THE INVENTION

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in an effort to moderate their disease causing or disease potentiating functions. Recently, however, attempts have been made to moderate the actual production of such proteins by interactions with messenger RNA (mRNA) or other intracellular RNA's that direct protein synthesis. It is generally the object of such therapeutic approaches to interfere with or otherwise modulate gene expression leading to undesired protein formation.

Antisense methodology is the complementary hybridization of relatively short oligonucleotides to single-stranded RNA or single-stranded DNA such that the normal, essential functions of these intracellular nucleic acids are disrupted. Hybridization is the sequence specific hydrogen bonding via Watson-Crick base pairs of the heterocyclic bases of oligonucleotides to RNA or DNA. Such base pairs are said to be complementary to one another.

Naturally occurring events that provide for the disruption of the nucleic acid function, as discussed by Cohen in *Oligonucleotides: Antisense Inhibitors of Gene Expression*, CRC Press, Inc., Boca Raton, Fla. (1989) are thought to be of two types. The first is hybridization arrest. This denotes the terminating event in which an oligonucleotide inhibitor binds to target nucleic acid and thus prevents, by simple steric hindrance, the binding of essential proteins, most often ribosomes, to the nucleic acid. Methyl phosphonate oligonucleotides (see, e.g., Miller, et al., *Anti-Cancer Drug Design* 1987, 2, 117) and α-anomer oligonucleotides are the two most extensively studied antisense agents that are thought to disrupt nucleic acid function by hybridization arrest.

In determining the extent of hybridization arrest of an oligonucleotide, the relative ability of an oligonucleotide to bind to complementary nucleic acids may be compared by determining the melting temperature of a particular hybridization complex. The melting temperature ($T_m$), a characteristic physical property of double helixes, denotes the temperature in degrees centigrade at which 50% helical (hybridized) versus coil (unhybridized) forms are present. $T_m$ is measured by using the UV spectrum to determine the formation and breakdown (melting) of hybridization. Base stacking which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing, i.e. base mismatch, has a strong destabilizing effect on the $T_m$.

The second type of terminating event for antisense oligonucleotides involves the enzymatic cleavage of the targeted RNA by intracellular RNase H. The mechanism of such RNase H cleavages requires that a 2'-deoxyribofuranosyl oligo-nucleotide hybridize to a targeted RNA. The resulting DNA-RNA duplex activates the RNase H enzyme; the activated enzyme cleaves the RNA strand. Cleavage of the RNA strand destroys the normal function of the RNA. Phosphorothioate oligo-nucleotides are one prominent example of antisense agents that operate by this type of terminating event. For a DNA oligonucleotide to be useful for activation of RNase H, the oligonucleotide must be reasonably stable to nucleases in order to survive in a cell for a time sufficient for the RNase H activation.

Several recent publications of Walder, et al. further describe the interaction of RNase H and oligonucleotides. Of particular interest are: (1) Dagle, et al., *Nucleic Acids Research* 1990, 18, 4751; (2) Dagle, et al., *Antisense Research And Development* 1991, 1, 11; (3) Eder, et al., *J. Biol. Chem.* 1991, 266, 6472; and (4) Dagle, et al., *Nucleic Acids Research* 1991, 19, 1805. In these papers, Walder, et al. note that DNA oligonucleotides having both unmodified phosphodiester internucleoside linkages and modified, phosphorothioate internucleoside linkages are substrates for cellular RNase H. Since they are substrates, they activate the cleavage of target RNA by the RNase H. However, the authors further note that in Xenopus embryos, both phosphodiester linkages and phosphorothioate linkages are also subject to exonuclease degradation. Such nuclease degradation is detrimental since it rapidly depletes the oligonucleotide available for RNase H activation.

As described in references (1), (2), and (4), to stabilize their oligonucleotides against nuclease degradation while still providing for RNase H activation, Walder, et al. constructed 2'-deoxy oligonucleotides having a short section of phosphodiester linked nucleotides positioned between sections of phosphoramidate, alkyl phosphonate or phosphotriester linkages. While the phosphoamidate-containing oligonucleotides were stabilized against exonucleases, in reference (4) the authors noted that each phosphoramidate linkage resulted in a loss of 1.6° C. in the measured $T_m$ value of the phosphoramidate containing oligonucleotides. Such decrease in the $T_m$ value is indicative of an undesirable decrease in the hybridization between the oligonucleotide and its target strand.

Other authors have commented on the effect such a loss of hybridization between an antisense oligonucleotide and its targeted strand can have. Saison-Behmoaras, et al., *EMBO Journal* 1991, 10, 1111, observed that even through an oligonucleotide could be a substrate for RNase H, cleavage efficiency by RNase H was low because of weak hybridization to the mRNA. The authors also noted that the inclusion of an acridine substitution at the 3' end of the oligonucleotide protected the oligonucleotide from exonucleases.

While it has been recognized that cleavage of a target RNA strand using an antisense oligonucleotide and RNase H would be useful, nuclease resistance of the oligonucleotide and fidelity of the hybridization are also of great importance. Heretofore, there have been no suggestion in the art of methods or materials that could both activate RNase H while concurrently maintaining or improving hybridization properties and providing nuclease resistance even though there has been a long felt need for such methods and materials. Accordingly, there remains a long-felt need for such methods and materials.

OBJECTS OF THE INVENTION

It is an object of this invention to provide oligonucleotides that both activate RNase H upon hybridization with a target strand and resist nuclease degradation.

It is a further object to provide oligonucleotides that activate RNase H, inhibit nuclease degradation, and provide improved binding affinity between the oligonucleotide and the target strand.

A still further object is to provide research and diagnostic methods and materials for assaying bodily states in animals, especially diseased states.

Another object is to provide therapeutic and research methods and materials for the treatment of diseases through modulation of the activity of DNA and RNA.

BRIEF DESCRIPTION OF THE INVENTION

In accordance with one embodiment of this invention there are provided oligonucleotides formed from a sequence of nucleotide units. The oligonucleotides incorporate a least one nucleotide unit that is functionalized to increase nuclease resistance of the oligonucleotides. Further, at least some of the nucleotide units of the oligonucleotides are functionalized with a substituent group to increase binding affinity of the oligonucleotides to target RNAS, and at least some of the nucleotide units have 2'-deoxy-erythro-pentofuranosyl sugar moieties.

In preferred oligonucleotides of the invention, nucleotide units that are functionalized for increased binding affinity are functionalized to include a 2'-substituent group. In even more preferred embodiments, the 2'-substituent group is fluoro, C1–C9 alkoxy, C1–C9 aminoalkoxy including aminopropoxy, allyloxy, $C_1$–$C_9$-alkyl-imidazole and polyethylene glycol. Preferred alkoxy substituents include methoxy, ethoxy and propoxy. A preferred aminoalkoxy unit is aminopropoxy. A preferred alkyl-imidazole is 1-propyl-3-(imidazoyl).

In certain preferred oligonucleotides of the invention having increased nuclease resistance, each nucleotide unit of the oligonucleotides is a phosphorothioate or phosphorodithioate nucleotide. In other preferred oligonucleotides, the 3' terminal nucleotide unit is functionalized with either or both of a 2' or a 3' substituent.

The oligonucleotides include a plurality of nucleotide units bearing substituent groups that increase binding affinity of the oligonucleotide to a complementary strand of nucleic acid. In certain preferred embodiments, the nucleotide units that bear such substituents can be divided into a first nucleotide unit sub-sequence and a second nucleotide unit sub-sequence, with 2'-deoxy-erythro-pentofuranosyl structures being positioned within the oligonucleotide between the first nucleotide unit sub-sequence and the second nucleotide unit sub-sequence. It is preferred that all such intervening nucleotide units be 2'-deoxy-erythro-pentofuranosyl units.

In further preferred oligonucleotides of the invention, nucleotide units bearing substituents that increase binding affinity are located at one or both of the 3' or the 5' termini of the oligonucleotide. There can be from one to about eight nucleotide units that are substituted with substituent groups. Preferably, at least five sequential nucleotide units are 2'-deoxy-erythro-pentofuranosyl sugar moieties.

The present invention also provides macromolecules formed from a plurality of linked nucleosides selected from α-nucleosides, β-nucleosides including 2'-deoxy-erythro-pentofuranosyl β-nucleosides, 4'-thionucleosides, and carbocyclic-nucleosides. These nucleosides are connected by linkages in a sequence that is hybridizable to a complementary nucleic acid. The linkages are selected from charged phosphorous linkages, neutral phosphorous linkages, and non-phosphorous linkages. The sequence of linked nucleosides is divided into at least two regions. The first nucleoside region includes the following types of nucleosides: α-nucleosides linked by charged and neutral 3'–5' phosphorous linkages; α-nucleosides linked by charged and neutral 2'–5' phosphorous linkages; α-nucleosides linked by non-phosphorous linkages; 4'-thionucleosides linked by charged and neutral 3'–5' phosphorous linkages; 4'-thionucleosides linked by charged and neutral 2'–5' phosphorous linkages; 4'-thionucleosides linked by non-phosphorous linkages; carbocyclic-nucleosides linked by charged and neutral 3'–5' phosphorous linkages; carbocyclic-nucleosides linked by charged and neutral 2'–5' phosphorous linkages; carbocyclic-nucleosides linked by non-phosphorous linkages; β-nucleosides linked by charged and neutral 2'–5' linkages; and β-nucleosides linked by non-phosphorous linkages. A second nucleoside region consists of 2'-deoxy-erythro-pentofuranosyl β-nucleosides linked by charged 3'–5' phosphorous linkages having negative charge at physiological pH. In preferred embodiments, the macromolecules include at least 3 of said 2'-deoxy-erythro-pentofuranosyl β-nucleosides, more preferably at least 5 of said 2'-deoxy-erythro-pentofuranosyl β-nucleotides. In further preferred embodiments there exists a third nucleoside region whose nucleosides are selected from those selectable for the first region. In preferred embodiments the second region is positioned between the first and third regions.

Preferred charged phosphorous linkages include phosphodiester, phosphorothioate, phosphorodithioate, phosphoroselenate and phosphorodiselenate linkages; phosphodiester and phosphorothioate linkages are particularly preferred. Preferred neutral phosphorous linkages include alkyl and aryl phosphonates, alkyl and aryl phosphoroamidites, alkyl and aryl phosphotriesters, hydrogen phosphonate and boranophosphate linkages. Preferred non-phosphorous linkages include peptide linkages, hydrazine linkages, hydroxy-amine linkages, carbamate linkages, morpholine linkages, carbonate linkages, amide linkages, oxymethyleneimine linkages, hydrazide linkages, silyl linkages, sulfide linkages, disulfide linkages, sulfone linkages, sulfoxide linkages, sulfonate linkages, sulfonamide linkages, formacetal linkages, thioformacetal linkages, oxime linkages and ethylene glycol linkages.

The invention also provides macromolecules formed from a plurality of linked units, each of which is selected from nucleosides and nucleobases. The nucleosides include α-nucleosides, β-nucleosides including 2'-deoxy-erythro-pento-furanosyl β-nucleosides, 4'-thionucleosides and carbocyclic-nucleosides. The nucleobases include purin-9-yl and pyrimidin-1-yl heterocyclic bases. The nucleosides and nucleobases of the units are linked together by linkages in a sequence wherein the sequence is hybridizable to a complementary nucleic acid and the sequence of linked units is divided into at least two regions. The linkages are selected from charged 3'–5' phosphorous, neutral 3'–5' phosphorous, charged 2'–5' phosphorous, neutral 2'–5' phosphorous or non-phosphorous linkages. A first of the regions includes nucleobases linked by non-phosphorous linkages and nucleobases that are attached to phosphate linkages via non-sugar tethering groups, and nucleosides selected from α-nucleosides linked by charged and neutral 3'–5' phosphorous linkages, α-nucleosides linked by charged and neutral 2'–5' phosphorous linkages, α-nucleosides linked by non-phosphorous linkages, 4'-thionucleosides linked by charged and neutral 3'–5' phosphorous linkages, 4'-thionucleosides linked by charged and neutral 2'–5' phosphorous linkages, 4'-thionucleosides linked by non-phosphorous linkages, carbocyclic-nucleosides linked by charged and neutral 3'–5' phosphorous linkages, carbocyclic-nucleosides linked by charged and neutral 2'–5' phosphorous linkages, carbocyclic-nucleosides linked by non-phosphorous linkages, β-nucleosides linked by charged and neutral 2'–5' linkages, and β-nucleosides linked by non-phosphorous linkages. A second of the regions includes only 2'-deoxy-erythro-pentofuranosyl β-nucleosides linked by charged 3'–5' phosphorous linkages wherein the 3'–5' phosphorous linkages have a negative charge at physiological pH.

In certain preferred embodiments, the first region includes at least two nucleobases joined by a non-phosphate linkage such as a peptide linkage. In preferred embodiments, the macromolecules include a third region that is selected from the same groups as described above for the first region. In preferred embodiments, the second region is located between the first and third regions.

The invention also provides macromolecules that have a plurality of linked units, each of which is selected from nucleosides and nucleobases. The nucleosides are selected from α-nucleosides, β-nucleosides, 4'-thionucleosides and carbo-cyclic-nucleosides and the nucleobases are selected from purin-9-yl and pyrimidin-1-yl heterocyclic bases. The nucleosides and nucleobases of said units are linked together by linkages in a sequence wherein the sequence is hybridizable to a complementary nucleic acid. The sequence of linked units is divided into at least two regions. The linkages are selected from charged phosphorous, neutral phosphorous or non-phosphorous linkages. A first of the regions include α-nucleosides linked by charged and neutral 3'–5' phosphorous linkages, α-nucleosides linked by charged and neutral 2'–5' phosphorous linkages, α-nucleosides linked by non-phosphorous linkages, 4'-thionucleosides linked by charged and neutral 3'–5' phosphorous linkages, 4'-thionucleosides linked by charged and neutral 2'–5' phosphorous linkages, 4'-thionucleosides linked by non-phosphorous linkages, carbocyclic-nucleosides linked by charged and neutral phosphorous linkages, carbocyclic-nucleosides linked by non-phosphorous linkages, β-nucleosides linked by charged and neutral 3'–5' linkages, β-nucleosides linked by charged and neutral 2'–5' linkages, and β-nucleosides linked by non-phosphorous linkages. A second of the regions include nucleobases linked by non-phosphorous linkages and nucleobases that are attached to phosphate linkages via a non-sugar tethering moiety.

Preferred nucleobases of the invention include adenine, guanine, cytosine, uracil, thymine, xanthine, hypoxanthine, 2-aminoadenine, 6-methyl and other alkyl adenines, 2-propyl and other alkyl adenines, 5-halo uracil, 5-halo cytosine, 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8 substituted adenines and 8-halo guanines, 8-amino guanine, 8-thiol guanine, 8-thiolalkyl guanines, 8-hydroxyl guanine and other 8 substituted guanines, other aza and deaza uracils, other aza and deaza thymidines, other aza and deaza cytosine, aza and deaza adenines, aza and deaza guanines or 5-trifluoromethyl uracil and 5-trifluorocytosine.

The invention also provides methods of treating an organism having a disease characterized by the undesired production of an protein. These methods include contacting the organism with an oligonucleotide having a sequence of nucleotides capable of specifically hybridizing to a complementary strand of nucleic acid where at least one of the nucleotides is functionalized to increase nuclease resistance of the oligonucleotide to nucleases, where a substituent group located thereon to increase binding affinity of the oligonucleotide to the complementary strand of nucleic acid and where a plurality of the nucleotides have 2'-deoxy-erythroregions; -pentofuranosyl sugar moieties.

Further in accordance with this invention there are provided compositions including a pharmaceutically effective amount of an oligonucleotide having a sequence of nucleotides capable of specifically hybridizing to a complementary strand of nucleic acid and where at least one of the nucleotides is functionalized to increase nuclease resistance of the oligonucleotide to nucleases and where a plurality of the nucleotides have a substituent group located thereon to increase binding affinity of the oligonucleotide to the complementary strand of nucleic acid and where a plurality of the nucleotides have 2'-deoxy-erythro-pentofuranosyl sugar moieties. The composition further include a pharmaceutically acceptable diluent or carrier.

Further in accordance with this invention there are provided methods for in vitro modification of a sequence specific nucleic acid including contacting a test solution containing an RNase H enzyme and said nucleic acid with an oligonucleotide having a sequence of nucleotides capable of specifically hybridizing to a complementary strand of nucleic acid and where at least one of the nucleotides is functionalized to increase nuclease resistance of the oligonucleotide to nucleases and where a plurality of the nucleotides have a substituent group located thereon to increase binding affinity of the oligonucleotide to the complementary strand of nucleic acid and where a plurality of the nucleotides have 2'-deoxy-erythro-pentofuranosyl sugar moieties.

There are also provided methods of concurrently enhancing hybridization and RNase H enzyme activation in an organism that includes contacting the organism with an oligonucleotide having a sequence of nucleotides capable of specifically hybridizing to a complementary strand of nucleic acid and where at least one of the nucleotides is functionalized to increase nuclease resistance of the oligonucleotide to nucleases and where a plurality of the nucleotides have a substituent group located thereon to increase binding affinity of the oligonucleotide to the complementary strand of nucleic acid and where a plurality of the nucleotides have 2'-deoxy- erythro-pentofuranosyl sugar moieties.

BRIEF DESCRIPTION OF THE DRAWINGS

This invention will be better understood when taken in conjunction with the drawings wherein.

DETAILED DESCRIPTION OF THE INVENTION

Figure 1:
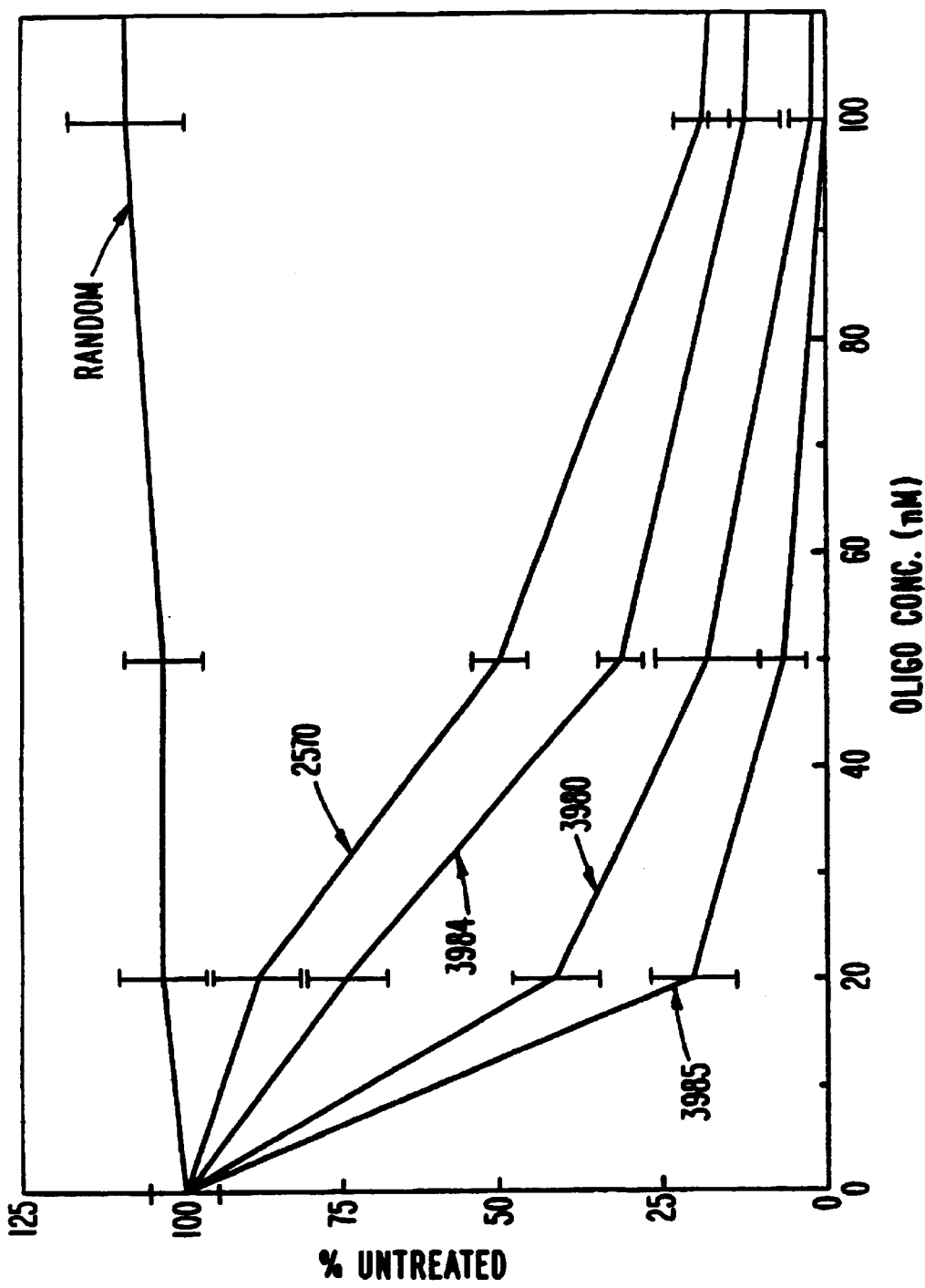
FIG. 1 is a graph showing dose response activity of oligonucleotides of the invention and a reference compound.

In accordance with the objects of this invention, novel oligonucleotides and macromolecules that, at once, have increased nuclease resistance, increased binding affinity to complementary strands and that are substrates for RNase H are provided. The oligonucleotides and macromolecules of the invention are assembled from a plurality of nucleotide, nucleoside or nucleobase sub-units. Each oligonucleotide or macromolecule of the invention includes at least one nucleotide, nucleoside or nucleobase unit that is functionalized to increase the nuclease resistances of the oligonucleotide. Further, in certain embodiments of the invention at least some of the nucleotide or nucleoside units bear a substituent group that increases the binding affinity of the oligonucleotide or macromolecule to a complementary strand of nucleic acid. Additionally at least some of the nucleotide units comprise a 2'-deoxy-erythro-pentofuranosyl group as their sugar moiety.

In conjunction with the above guidelines, each nucleotide unit of an oligonucleotides of the invention, alternatively referred to as a subunit, can be a "natural" or a "synthetic" moiety. Thus, in the context of this invention, the term "oligonucleotide" in a first instance refers to a polynucleotide formed from a plurality of joined nucleotide units. The nucleotides units are joined together via native internucleoside, phosphodiester linkages. The nucleotide units are formed from naturally-occurring bases and pentofuranosyl sugars groups. The term "oligonucleotide" thus effectively includes naturally occurring species or synthetic species formed from naturally occurring nucleotide units.

Oligonucleotides of the invention also can include modified subunits. The modifications can occur on the base portion of a nucleotide, on the sugar portion of a nucleotide or on the linkage joining one nucleotide to the next. In addition, nucleoside units can be joined via connecting groups that substitute for the inter-nucleoside phosphate linkages. Macromolecules of the type have been identified as oligonucleosides. In such oligonucleosides the linkages include an —O—CH$_2$—CH$_2$—O— linkage (i.e., an ethylene glycol linkage) as well as other novel linkages disclosed in the following U.S. patent applications: Ser. No. 566,836, filed Aug. 13, 1990, entitled Novel Nucleoside Analogs (now U.S. Pat. No. 5,223,618); Ser. No. 703,619, filed May 21, 1991, entitled Backbone Modified Oligonucleotide Analogs (now U.S. Pat. No. 5,378,825); and Ser. No. 903,160, filed Jun. 24, 1992, entitled Heteroatomic Oligonucleotide Linkage (now U.S. Pat. No. 5,623,070). Other modifications can be made to the sugar, to the base, or to the phosphate group of the nucleotide. Representative modifications are disclosed in the following U.S. patent applications: Ser. No. 463,358, filed Jan. 11, 1990, entitled Compositions And Methods For Detecting And Modulating RNA Activity; Ser. No. 566,977, filed Aug. 13, 1990, entitled Sugar Modified oligonucleotides That Detect And Modulate Gene Expression; Ser. No. 558,663, filed Jul. 27, 1990, entitled Novel Polyamine Conjugated Oligonucleotides (now U.S. Pat. No. 5,138,045); Ser. No. 558,806, filed Jul. 27, 1991, entitled Nuclease Resistant Pyrimidine Modified Oligonucleotides That Detect And Modulate Gene Expression; and Ser. No. PCT/US91/00243, filed Jan. 11, 1991, entitled Compositions and Methods For Detecting And Modulating RNA Activity, all assigned to the assignee of this invention. The disclosures of each of the above noted patent applications are herein incorporated by reference.

Thus, the terms oligonucleotide is intended to include naturally occurring structures as well as non-naturally occurring or "modified" structures—including modified sugar moieties, modified base moieties or modified sugar linking moieties—that function similarly to natural bases, natural sugars and natural phosphodiester linkages. Thus, oligonucleotides can have altered base moieties, altered sugar moieties or altered inter-sugar linkages. Exemplary among these are phosphorothioate, phosphorodithioate, methyl phosphonate, phosphotriester, phosphoramidate, phosphoroselenate and phosphorodiselenate inter-nucleoside linkages used in place of phosphodiester inter-nucleoside linkages; deaza or aza purines and pyrimidines used in place of natural purine and pyrimidine bases; pyrimidine bases having substituent groups at the 5 or 6 position; purine bases having altered or replacement substituent groups at the 2, 6 or 8 positions; or sugars having substituent groups at their 2' position, substitutions for one or more of the hydrogen atoms of the sugar, or carbocyclic or acyclic sugar analogs. They may also comprise other modifications consistent with the spirit of this invention. Such oligonucleotides are best described as being functionally interchangeable with natural oligonucleotides (or synthesized oligonucleotides along natural lines), but which have one or more differences from natural structure. All such oligonucleotides are comprehended by this invention so long as they function effectively to mimic the structure of a desired RNA or DNA strand.

In one preferred embodiment of this inventions nuclease resistance is achieved by utilizing phosphorothioate internucleoside linkages. Contrary to the reports of Walder, et al. note above, I have found that in systems such as fetal calf serum containing a variety of 3'-exonucleases, modification of the internucleoside linkage from a phosphodiester linkage to a phosphorothioate linkage provides nuclease resistance.

Brill, et al., *J. Am. Chem. Soc.* 1991, 113, 3972, recently reported that phosphorodithioate oligonucleotides also exhibit nuclease resistance. These authors also reported that phosphorodithioate oligonucleotide bind with complementary deoxyoligonucleotides, stimulate RNase H and stimulate the binding of lac repressor and cro repressor. In view of these properties, phosphorodithioates linkages also may be useful to increase nuclease resistance of oligonucleotides of the invention.

Nuclease resistance further can be achieved by locating a group at the 3' terminus of the oligonucleotide utilizing the methods of Saison-Behmoraras, et al., supra, wherein a dodecanol group is attached to the 3' terminus of the oligonucleotide. Other suitable groups for providing increased nuclease resistance may include steroid molecules and other lipids, reporter molecules, conjugates and non-aromatic lipophilic molecules including alicyclic hydrocarbons, saturated and unsaturated fatty acids, waxes, terpenes and polyalicyclic hydrocarbons including adamantane and buckmin-sterfullerenes. Particularly useful as steroid molecules for this purpose are the bile acids including cholic acid, deoxycholic acid and dehydrocholic acid. Other steroids include cortisone, digoxigenin, testosterone and cholesterol and even cationic steroids such as cortisone having a trimethylaminomethyl hydrazide group attached via a double bond at the 3 position of the cortisone ring. Particularly useful reporter molecules are biotin and fluorescein dyes. Such groups can be attached to the 2' hydroxyl group or 3' hydroxyl group of the 3' terminal nucleotide either directly or utilizing an appropriate connector in the manner described in U.S. patent application Ser. No. 782,374, filed Oct. 24, 1991 entitled Derivatized Oligonucleotides Having Improved Uptake and Other Properties, assigned to the assignee as this application, the entire contents of which are herein incorporated by reference.

Attachment of functional groups at the 5' terminus of compounds of the invention also may contribute to nuclease resistance. Such groups include acridine groups (which also serves as an intercalator) or other groups that exhibit either beneficial pharmacokinetic or pharmacodynamic properties. Groups that exhibit pharmacodynamic properties, in the context of this invention, include groups that improve oligonucleotide uptake, enhance oligonucleotide resistance to degradation, and/or strengthened sequence-specific hybridization with RNA. Groups that exhibit pharmacokinetic properties, in the context of this invention, include groups that improve oligonucleotide uptake, distribution, metabolism or excretion.

Further nuclease resistance is expect to be conferred utilizing linkages such as the above identified —O—CH$_2$—CH$_2$—O— linkage and similar linkages of the above identified U.S. patent applications Ser. No. 566,836, Ser. No. 703,619, and Ser. No. 903,160, since these types of linkages do not utilize natural phosphate ester-containing backbones that are the natural substrates for nucleases. When nuclease resistance is conferred upon an oligonucleotide of the invention by the use of a phosphorothioate or other nuclease resistant internucleotide linkages, such linkages will reside in each internucleotide sites. In other embodiments, less than all of the internucleotide linkages will be modified to phosphorothioate or other nuclease resistant linkages.

I have found that binding affinity of oligonucleotides of the invention can be increased by locating substituent groups on nucleotide subunits of the oligonucleotides of the invention. Preferred substituent groups are 2' substituent groups, i.e., substituent groups located at the 2' position of the sugar moiety of the nucleotide subunits of the oligonucleotides of the invention. Presently preferred substituent groups include but are not limited to 2'-fluoro, 2'-alkoxy, 2'-amino-alkoxy, 2'-allyloxy, 2'-imidazole-alkoxy and 2'-poly(ethylene oxide). Alkoxy and aminoalkoxy groups generally include lower alkyl groups, particularly C1–C9 alkyl. Poly(ethylene glycols) are of the structure (O—CH$_2$—CH$_2$)$_n$—O-alkyl. Particularly preferred substituent groups are 2'-fluoro, 2'-methoxy, 2'-ethoxy, 2'-propoxy, 2'-aminopropoxy, 2'-imidazolepropoxy, 2'-imidazolebutoxy, and 2'-allyloxy groups.

Binding affinity also can be increased by the use of certain modified bases in the nucleotide units that make up the oligonucleotides of the invention. Such modified bases may include 6-azapyrimidines and N-2, N-6 and 0-6 substituted purines including 2-aminopropyladenine. Other modified pyrimidine and purine base are expected to increase the binding affinity of oligonucleotides to a complementary strand of nucleic acid.

The use of 2'-substituent groups increases the binding affinity of the substituted oligonucleotides of the invention. In a published study, Kawasaki and Cook, et al., *Synthesis and Biophysical Studies of 2'-dRIBO-F Modified Oligonucleotides*, Conference On Nucleic Acid Therapeutics, Clearwater, Fla., Jan. 13, 1991, the inventor has reported a binding affinity increase of 1.6° C. per substituted nucleotide unit of the oligonucleotide. This is compared to an unsubstituted oligonucleotide for a 15 mer phosphodiester oligonucleotide having 2'-deoxy-2'-fluoro groups as a substituent group on five of the nucleotides of the oligonucleotide. When 11 of the nucleotides of the oligonucleotide bore such 2'-deoxy-2'-fluoro substituent groups, the binding affinity increased to 1.8° C. per substituted nucleotide unit.

In that same study, the 15 mer phosphodiester oligonucleotide was derivatized to the corresponding phosphorothioate analog. When the 15 mer phosphodiester oligonucleotide was compared to its phosphorothioate analog, the phosphorothioate analog had a binding affinity of only about 66% of that of the 15 mer phosphodiester oligonucleotide. Stated otherwise, binding affinity was lost in derivatizing the oligonucleotide to its phosphorothioate analog. However, when 2'-deoxy-2'-fluoro substituents were located at 11 of the nucleotides of the 15 mer phosphorothioate oligonucleotide, the binding affinity of the 2'-substituent groups more than overcame the decrease noted by derivatizing the 15 mer oligonucleotide to its phosphorothioate analog. In this compound, i.e., a 15 mer phosphorothioate oligonucleotide having 11 nucleotide substituted with 2'-fluoro groups, the binding affinity was increased to 2.5° C. per substituent group. In this study no attempt was made to include an appropriate consecutive sequence of nucleotides have 2'-deoxy-erythro-pentofuranosyl sugars that would elicit RNase H enzyme cleavage of a RNA target complementary to the oligonucleotide of the study.

In order to elicit RNase H enzyme cleavage of a target RNA, an oligonucleotide of the invention must include a segment or sub-sequence therein that is a DNA type segment. Stated otherwise, at least some of the nucleotide subunits of the oligonucleotides of the invention must have 2'-deoxy-erythro-pentofuranosyl sugar moieties. I have found that a sub-sequence having more than three consecutive, linked 2'-deoxy-erythro-pentofuranosyl-containing nucleotide sub-units likely is necessary in order to elicit RNase H activity upon hybridization of an oligonucleotide of the invention with a target RNA. It is presently preferred to have a sub-sequence of 5 or more consecutive 2'-deoxy-erythro-pentofuranosyl containing nucleotide sub-units in an oligonucleotide of the invention. Use of at least 7 consecutive 2'-deoxy-erythro-pentofuranosyl-containing nucleotide subunits is particularly preferred.

The mechanism of action of RNase H is recognition of a DNA-RNA duplex followed by cleavage of the RNA stand of this duplex. As noted in the Background section above, others in the art have used modified DNA strands to impart nuclease stability to the DNA strand. To do this they have used modified phosphate linkages impart increased nuclease stability but detract from hybridization properties. While I do not wish to be bound by theory, I have identified certain nucleosides or nucleoside analogs that will impart nuclease stability to an oligonucleotide, oligonucleoside or other macromolecule and in certain instances also impart increase binding to a complementary strand. These include α-nucleosides linked by charged and neutral 3'–5' phosphorous linkages, α-nucleosides linked by charged and neutral 2'–5' phosphorous linkages, α-nucleosides linked by non-phosphorous linkages, 4'-thionucleosides linked by charged and neutral 3'–5' phosphorous linkages, 4'-thionucleosides linked by charged and neutral 2'–5' phosphorous linkages, 4'-thionucleosides linked by non-phosphorous linkages, carbocyclic-nucleosides linked by charged and neutral phosphorous linkages, carbocyclic-nucleosides linked by non-phosphorous linkages, β-nucleosides linked by charged and neutral 3'–5' linkages, β-nucleosides linked by charged and neutral 2'–5' linkages, and β-nucleosides linked by non-phosphorous linkages. They further include nucleobases that are attached to phosphate linkages via non-sugar tethering groups or are attached to non-phosphate linkages.

Again, while not wishing to be bound by any particular theory, I have found certain criteria that must be met for RNase H to recognize and elicit cleavage of a RNA strand.

The first of these is that the RNA stand at the cleavage site must have its nucleosides connected via a phosphate linkage that bears a negative charge. Additionally, the sugar of the nucleosides at the cleavage site must be a β-pentofuranosyl sugar and also must be in a 2' endo conformation. The only nucleosides (nucleotides) that fit this criteria are phosphodiester, phosphorothioate, phosphorodithioate, phosphoroselenate and phosphorodiselenate nucleotides of 2'-deoxy-erythro-pentofuranosyl β-nucleosides.

In view of the above criteria, even certain nucleosides that have been shown to reside in a 2' endo conformation (e.g., cyclopentyl nucleosides) will not elicit RNase H activity since they do not incorporate a pentofuranosyl sugar. Modeling has shown that oligonucleotide 4'-thionucleosides also will not elicit RNase H activity, even though such nucleosides reside in an envelope conformation, since they do not reside in a 2' endo conformation. Additionally, since α-nucleosides are of the opposite configuration from β-pentofuranosyl sugars they also will nct elicit RNase H activity.

Nucleobases that are attached to phosphate linkages via non-sugar tethering groups or via non-phosphate linkages also do not meet the criteria of having a β-pentofuranosyl sugar in a 2' endo conformation. Thus, they likely will not elicit RNase H activity.

As used herein, α and β nucleosides include ribofuranosyl, deoxyribofuranosyl (2'-deoxy-erythropentofuranosyl) and arabinofuranosyl nucleosides. 4'-Thionucleosides are nucleosides wherein the 4' ring oxygen atom of the pento-furanosyl ring is substituted by a sulfur atom. Carbocyclic nucleosides are nucleosides wherein the ring oxygen is substituted by a carbon atom. Carbocyclic nucleosides include cyclopropyl, cyclobutyl, cyclopentyl and cyclohexyl rings ($C_3$–$C_6$-carbocyclic) having an appropriate nucleobase attached thereto. The above α and β nucleosides, 4'-thionucleosides and carbocyclic nucleosides can include additional functional groups on their heterocyclic base moiety and additional functional groups on those carbon atoms of sugar or carbocyclic moiety that are not utilized in linking the nucleoside in a macromolecule of the invention. For example, substituent groups can be placed on the 1, 2, 3, 6, 7 or 8 position of purine heterocycles, the 2, 3, 4, 5 or 6 position of pyrimidine heterocycles. Deaza and aza analogs of the purine and pyrimidine heterocycles can be selected or 2' substituted sugar derivatives can be selected. All of these types of substitutions are known in the nucleoside art.

α-Nucleosides have been incorporated into oligonucleotides; as reported by Gagnor, et. al., *Nucleic Acids Research* 1987, 15, 10419, they do not support RNase H degradation. Carbocyclic modified oligonucleotides have been synthesized by a number of investigators, including Perbost, et al., *Biochemical and Biophysical Research Communications* 1989, 165, 742; Sagi, et al., *Nucleic Acids Research* 1990, 18, 2133; and Szemzo, et. al., *Tetrahedron Letters* 1990, 31, 1463. 4'-Thionucleosides have been known for at least 25 years. An improved synthesis via 4'-thioribofuranose recently was reported by Secrist, et. al., *Tenth International Roundtable: Nucleosides, Nucleotides and Their Biological Evaluation*, Sep. 16–20, 1992, Abstracts of Papers, Abstract 21 and in published patent application PCT/US91/02732.

For incorporation into oligonucleotides or oligonucleotide suggorates, α and β nucleosides, 4'-thionucleosides and carbocyclic nucleosides will be blocked in the 5' position (or the equivalent to the 5' position for the carbocyclic nucleosides) with a dimethoxytrityl group, followed by phosphitylation in the 3' position as per the tritylation and phosphitylation procedures reported in *Oligonucleotides and Analogs, A Practical Approach*, Eckstein, F., Ed.; The Practical Approach Series, IRL Press, New York, 1991. Incorporation into oligonucleotides will be accomplished utilizing a DNA synthesizer such as an ABI 380 B model synthesizer using appropriate chemistry for the formation of phosphodiester, phosphorothioate, phosphorodithioate or methylphosphonates as per the synthetic protocols illustrated in Eckstein op. cit.

Boranophosphate linked oligonucleotides are prepared as per the methods described in published patent application PCT/US/06949. Phosphoroselenates and phosphorodiselenates linked oligonucleotides are prepared in a manner analogous to their thio counterparts using the reagent 3H-1, 2-benzothia-seleno-3-ol for introducing the seleno moiety. This reagent is also useful for preparing selenothiophosphates from corresponding H-phosphonothiate diester as reported by Stawinski, et al. *Tenth International Roundtable: Nucleosides, Nucleotides and Their Biological Evaluation*, Sep. 16–20, 1992, Abstracts of Papers, Abstract 80. Hydrogen phosphonate-linked oligonucleotides—as well as alkyl and aryl phosphonate, alkyl and aryl phosphotriesters and alkyl and aryl phosphoramidates linked oligonucleotides—are prepared in the manner of published patent application PCT/US88/03842. This patent application also discusses the preparation of phosphorothioates and phosphoroselenates linked oligonucleotides Non-phosphate backbones include carbonate, carbamate, silyl, sulfide, sulfone, sulfoxide, sulfonate, sulfonamide, formacetal, thioformacetal, oxime, hydroxylamine, hydrazine, hydrazide, disulfide, amide, urea and peptide linkages. oligonucleoside having their nucleosides connected by carbonate linkages are prepared as described by, for example, Mertes, et al., *J. Med. Chem.* 1969, 12, 154 and later by others. Oligonucleoside having their nucleosides connected by carbamate linkages are prepared as was first described by Gait, et. al., *J. Chem. Soc. Perkin* 1 1974, 1684 and later by others. Oligonucleoside having their nucleosides connect by silyl linkages are prepared as described Ogilvie, et al., *Tetrahedron Letters* 1985, 26, 4159 and *Nucleic Acids Res.* 1988, 16, 4583. Oligonucleoside having their nucleosides connected by sulfide linkages and the associated sulfoxide and sulfone linkages are prepared as described by Schneider, et al., *Tetrahedron Letters* 1990, 31, 335 and in other publications such as published patent application PCT/US89/02323.

Oligonucleoside having their nucleosides connected by sulfonate linkages are prepared as described by Musicki, et al., *Org. Chem.* 1991, 55, 4231 and *Tetrahedron Letters* 1991, 32, 2385. Oligonucleoside having their nucleosides connected by sulfonamide linkages are prepared as described by Kirshenbaum, et. al., *The 5th San Diego Conference: Nucleic Acids: New Frontiers*, Poster abstract 28, Nov. 14–16, 1990. Oligonucleoside having their nucleosides connected by formacetals are prepared as described by Matteucci, *Tetrahedron Letters* 1990, 31, 2385 and Veeneman, et. al., *Recueil des Trav. Chim.* 1990, 109, 449 as well as by the procedures of published patent application PCT/US90/06110. Oligonucleoside having their nucleosides connected by thioformacetals are prepared as described by Matteucci, et. al., *J. Am. Chem. Soc.* 1991, 113, 7767; Matteucci, *Nucleosides & Nucleotides* 1991, 10, 231, and the above noted patent application PCT/US90/06110.

Oligonucleoside having their nucleosides connected by oxime, hydroxylamine, hydrazine and amide linkages will be prepared as per the disclosures of U.S. patent application Ser. No. 703,619 filed May 21, 1991 (now U.S. Pat. No. 5,378,825), and related PCT patent applications PCT/US92/04292 and PCT/US92/04305 as well as corresponding published procedures by myself and co-authors in Vasseur, et. al., *J. Am. Chem. Soc.* 1992, 114, 4006 and Debart, et. al., *Tetrahedron Letters* 1992, 33, 2645. Oligonucleoside having their nucleosides connect by morpholine linkages will be prepared as described in U.S. Pat. No. 5,034,506.

Further non-phosphate linkage suitable for use in this invention include linkages have two adjacent heteroatoms in combination with one or two methylene moieties. Oligonucleosides having their nucleosides connect by such linkages will be prepared as per the disclosures of U.S. patent application Ser. No. 903,160 (now U.S. Pat. No. 5,623,070), filed Jun. 24, 1992, the entire disclosure of which is herein incorporated by reference.

Structural units having nucleobases attached via non-phosphate linkages wherein the non-phosphate linkages are peptide linkages will be prepared as per the procedures of patent application PCT/EP/01219. For use in preparing such structural units, suitable nucleobase include adenine, guanine, cytosine, uracil, thymine, xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thiolalkyl, hydroxyl and other 8 substituted adenines and guanines, 5-trifluoromethyl and other 5 substituted uracils and cytosines, 7-methylguanine and other nucleobase such as those disclosed in U.S. Pat. No. 3,687,808.

Peptide linkages include 5, 6 and 7 atom long backbones connected by amide links. Other, similar non-phosphate backbones having ester, amide and hydrazide links are prepared as per published patent applications PCT/US86/00544 and PCT/US86/00545.

Other $\alpha$ and $\beta$ nucleosides, 4'-thionucleoside and carbocyclic nucleosides having the heterocyclic bases as disclosed for the nucleobases above can be prepared and incorporated in to the respective $\alpha$ and $\beta$ nucleosides, 4'-thionucleoside and carbocyclic nucleosides.

Non-sugar tethering groups include 3,4-dihydroxybutyl (see, Augustyns, et. al., *Nucleic Acids Research* 1991, 19, 2587) and dihydroxyproproxymethyl (see, Schneider, et al., *J. Am. Chem. Soc.* 1990, 112, 453) and other linear chains such as $C_1$–$C_{10}$ alkyl, alkenyl and alkynyl. While the 3,4-dihydroxybutyl and dihydroxyproproxymethyl non-sugar tethering groups are the acyclic fragments of a $\beta$-pentofuranosyl sugar, they will not serve to elicit RNase H activation. Preferred for a non-sugar tethering groups is the 3,4-dihydroxybutyl groups since the dihydroxyproproxymethyl when used in an oligonucleotide analog upon hybridization has shown a suppression of the melting temperature between it and a complementary nucleic strand.

Normal 3'–5' phosphodiester linkages of natural nucleic acids have 3 hetero atoms (—O—P—O—) between the respective sugars of the adjacent nucleosides. If the 5' methylene group (the 5' $CH_2$ group of the 3' nucleoside of the adjacent nucleosides) is also included, these phosphodiester linked nucleic acids can be viewed as being connected via linkages that are 4 atoms long.

Two strands of $\beta$-oligonucleotides will hybridize with each other with an anti-parallel polarity while a strand of $\alpha$-oligonucleotides will hybridize with strand of $\beta$-oligonucleotides with a parallel polarity. In certain embodiments, oligonucleotides of the invention will have a region formed of $\alpha$-nucleotides and a further region formed of $\beta$-nucleotides. These two regions are connected via an inter-region linkage. For such an oligonucleotide to bind to a corresponding complementary $\beta$ strand of a nucleic acid and maintain the parallel polarity of the $\alpha$ region simultaneously with the anti-parallel polarity of the $\beta$ region, either a 3'—3' connection or a 5'—5' connection must be made between the $\alpha$ and $\beta$ regions of the oligonucleotide of the invention. The 3'—3' connection (having no 5' methylene moieties) yields a 3 atom long linkage, while the 5'—5' connection (having two 5' methylene moieties) yields a 5 atom long linkage.

For embodiments of the invention wherein a 4 atom long linkage between adjacent $\alpha$ and $\beta$ regions is desired, use of a symmetrical linking nucleoside or nucleoside surrogate will yield a 4 atom long linkage between each adjacent nucleoside pair. An example of such a symmetrical linking nucleoside surrogate is a 3,3-bis-hydroxylmethyl cyclobutyl nucleoside as disclosed in my U.S. patent application Ser. No. 808,201, filed Dec. 13, 1991, entitled Cyclobutyl Oligonucleotide Surrogates (now U.S. Pat. No. 5,359,044), the entire disclosure of which is herein incorporated by reference.

Other suitable linkages to achieve 4 atom spacing will include alicyclic compounds of the class 1-hydroxyl-2-hydroxyl-methyl-alk-$\omega$-yl type moieties wherein a nucleobase is connected to the $\omega$ (omega or last) position. Examples of this type of linkage are 9-(1-hydroxyl-2-methylhydroxyl-pent-5-yl)adenine, 9-(1-hydroxyl-2-methylhydroxyl-pent-5-yl)guanine, 1-(1-hydroxyl-2-methylhydroxyl-pent-5-yl) uridine, 1-(1-hydroxyl-2-methylhydroxyl-pent-5-yl)cytosine and the corresponding 3, 4 and 7 atom analogs, wherein a propyl, butyl or hexyl alkyl group is utilized in place of the pentyl group. A further example includes a nucleoside having a pentofuranosyl sugar that is substituted with a 4'-hydroxylmethy group. In this instance the linkages to the 5' nucleoside is an normal linkage via the normal 5' hydroxyl moiety, whereas the linkage to the 3' nucleoside is not through the normal 3'-hydroxyl group but is through the 4'-hydroxylmethy moiety. As with the cyclobutyl nucleoside, with both the alicyclic moieties or the 4'-substituted nucleoside moieties, a 4 atom long linkage is achieved between adjacent regions of the oligonucleotide of the invention.

In a manner similar to that described above, in those embodiments of this invention that have adjacent regions of a macromolecule formed from different types of moieties, an interconnection of a desired length can be formed between each of the two adjacent regions of the macromolecule. The symmetrical interconnection is achieved hy selecting a linking moiety that can form a covalent bond to both of the different types of moieties forming the adjacent regions. The linking moiety is selected such that the resulting chain of atoms between the linking moiety and the different types of moieties is of the same length.

The oligonucleotides and macromolecules of the invention preferably comprise from about 10 to about 30 nucleotide or nucleobase subunits. It is more preferred that such oligonucleotides and macromolecules comprise from about 15 to about 25 subunits. As will be appreciated, a subunit is a base and sugar combination suitably bound to adjacent subunits through phosphorothioate or other linkages or a nucleobase and appropriate tether suitable bound to adjacent subunits through phosphorous or non-phosphorous linkages. Such terms are used interchangeably with the term "unit." In order to elicit a RNase H response, as specified above, within this total overall sequence length of the oligonucleotide or macromolecule will be a sub-sequence of greater than 3 but preferably five or more consecutive 2'-deoxy-erythro-pentofuranosyl containing nucleotide subunits.

It is presently preferred to incorporated the 2'-deoxy-erythro-pentofuranosyl-containing nucleotide sub-sequence within the oligonucleotide or macromolecule main sequence such that within the oligonucleotide or macromolecule other nucleotide subunits of the oligonucleotide or macromolecule are located on either side of the 2'-deoxy-erythro-pentofuranosyl nucleotide sub-sequence.

In certain embodiments of the invention, if the remainder of the nucleotide subunits each include a 2'-substituent group for increased binding affinity, then the 2'-deoxy-erythro-pentofuranosyl nucleotide sub-sequence will be located between a first sub-sequence of nucleotide subunits having 2'-substituent groups and a second sub-sequence of nucleotide subunits having 2'-substituent groups. Other constructions are also possible, including locating the 2'-deoxy-erythro-pentofuranosyl nucleotide sub-sequence at either the 3' or the 5' terminus of the oligonucleotide of the invention.

Compounds of the invention can be utilized in diagnostics, therapeutics and as research reagents and kits. They can be utilized in pharmaceutical compositions by including an effective amount of oligonucleotide of the invention admixed with a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of nucleic acid that codes for the undesirable protein.

Such therapeutic treatment can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to such therapeutic and/or prophylactic treatment. Seemingly diverse organisms such as bacteria, yeast, protozoa, algae, all plant and all higher animal forms, including warm-blooded animals, can be treated by this therapy. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g., mitochondria and chloroplasts, of eukaryotic cells also include transcription and translation mechanisms. As such, single cells, cellular populations or organelles also can be included within the definition of organisms that are capable of being treated with the therapeutic or diagnostic oligo-nucleotides of the invention. As used herein, therapeutics is meant to include both the eradication of a disease state, killing of an organism, e.g., bacterial, protozoan or other infection, or control of erratic or harmful cellular growth or expression.

For purpose of illustration, the compounds of the invention have been used in a ras-luciferase fusion system using ras-luciferase transactivation. As described in U.S. patent application Ser. No. 07/715,196, filed Jun. 14, 1991, entitled Antisense Inhibition of RAS Oncogene and assigned commonly with this application, the entire contents of which are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon 12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

The following examples and procedures illustrate the present invention and are not intended to limit the same.

EXAMPLE 1

Oligonucleotide synthesis

Unsubstituted and substituted oligonucleotides were synthesized on an automated DNA synthesizer (Applied Biosystems model 380B) using standard phosphoramidate chemistry with oxidation by iodine. For phosphorothioate oligonucleotides, the standard oxidation bottle was replaced by 0.2 M solution of 3H-1,2-benzodithiole-3-one 1,1-dioxide in acetonitrile for the step wise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitation twice out of 0.5 M NaCl solution with 2.5 volumes ethanol. Analytical gel electrophoresis was accomplished in 20% acrylamide, 8 M urea, 454 mM Tris-borate buffer, pH=7.0. Oligonucleotides and phosphorothioates were judged from polyacrylamide gel electrophoresis to be greater than 80% full-length material.

EXAMPLE 2 oligonucleotide Having a Oligonucleotide Regions Flanking Central β Oligonucleotide Region A. α-β Mixed oligonucleotide having non-symmetricai 3'—3' and 5'—5' linkages For the preparation of a 15 mer, a first region 4 nucleotides long of an α oligonucleotide is prepared as per the method of Gagnor, et. al., *Nucleic Acids Research* 1987, 15, 10419 or on a DNA synthesizer utilizing the general protocols of Example 1. Preparation is from the 5' direction towards the 3' direction. The terminal 3' hydroxyl groups is deprotected. A normal β region of a DNA oligonucleotide 7 nucleotides long is added in a 3' to 5' direction terminating in a free 5' hydroxyl group. A further 4 nucleotide long region of α nucleotides is then added in a 5' to 3' direction. The resulting 15 mer mixed α-β-α oligonucleotide includes a 3 atom 3'—3' linkage between the first α region and the β region and a 5 atom 5'—5' linkage between the second α region and the β region.

B. α-β Mixed oligonucleotide having non-symmetrical 3'—3' and 5'—5' linkages

The procedure of Example 2-A is repeated except the intermediate β region is added as a phosphorothioate region by substitution a thiation step for the normal oxidization step. Thiation is conducted via use of the Beaucage Reagent, i.e., the 1,2-benzodithiole-3-one 1,1-dioxide of Example 1.

C. α-β Mixed oligonucleotide having symmetrical 4 atom linkages

For the preparation of a 17 mer, a first region 4 nucleotides long is of an α-oligonucleotide is prepared on the DNA synthesizer as per the method of Gagnor, et. al., *Nucleic Acids Research* 1987, 15, 10419. Preparation is from the 5' direction towards the 3' direction. The terminal 3' hydroxyl groups is deprotected. A single nucleoside surrogate unit, 1α-thymidyl-3β-hydroxymethyl-3α-methoxytrityloxymethyl-cyclobutane amidite (prepared as per U.S. patent application Ser. No. 808,201, identified above) is condensed on the terminal 3' hydroxyl group of the α-oligonucleotide region in the normal manner as per Example 1. The trityl hydroxyl group blocking group of the cyclobutyl thymidine nucleoside surrogate is deblocked. A 7 nucleotide region of phosphorothioate 2'-deoxy β-nucleotide sequence is added on the synthesizer. Upon completion of the DNA region of the macromolecule a 1α-thymidyl-2β-hydroxy-3α-methoxytrityloxycyclobutane unit activated as a normal phosphoramidite on the 2 hydroxy will be condensed on the growing macromolecule in the same manner as is the 1α-thymidyl-3β-hydroxymethyl-3α-methoxytrityloxymethyl-cyclobutane moiety above. Following deblocking of the trityl blocking group of the nucleoside surrogate unit, a further 4 nucleotide stretch of α-oligonucleotides is added to complete the macromolecule. Deblocking, removal from the support and purification of the resulting macromolecule is conducted in the normal manner.

EXAMPLE 3 oligonucleotide Having 2'-substituted Oligonucleotides Regions Flanking Central 2'-Deoxy Phosphorothioate oligonucleotide Region A 15 mer RNA target of the sequence 5'GCG TTT TTT TTT TGC G 3' (SEQ. ID NO: 11) was prepared in the normal manner on the DNA sequencer using RNA protocols. A series of phosphorothioate complementary oligonucleotides having 2'-O-substituted nucleotides in regions that flank 2'-deoxy region are prepared utilizing 2'-O-substituted nucleotide precursor prepared as per known literature preparations, i.e., 2'-O-methyl, or as per the procedures of PCT application PCT/US91/05720 or U.S. patent applications Ser. Nos. 566,977 or 918,362. The 2'-O-substituted nucleotides are added as their 5'-O-dimethoxytrityl-3'-phosphoramidites in the normal manner on the DNA synthesizer. The complementary oligonucleotides have the sequence of 5' CGC AAA AAA AAA AAA ACG C 3' (SEQ. ID NO:11). The 2'-O-substituent was located in CGC and CG regions of these oligonucleotides. The following 2'-O-substituents are used: 2'-fluoro; 2'-O-methyl; 2'-O-propyl; 2'-O-allyl; 2'-O-aminopropoxy; 2'-O-(methoxyethoxyethyl), 2'-O-imidazolebutoxy and 2'-O-imidazolepropoxy. Additionally the same sequence is prepared in both as a phosphodiester and a phosphorothioate. Following synthesis the test compounds and the target compound are subjected to a melt analysis to measure their Tm's and nuclease resistance as per the protocols in the above referenced PCT application PCT/US91/05720. The test sequences were found not to be substrates for RNase H whereas as the corresponding target sequence is. These test sequences will be nuclease stable and will have increase binding affinity to the target compared to the phosphodiester analogue.

EXAMPLE 4 oligonucleotide Having 2'-5' Phosphodiester oligonucleotide Regions Flanking A Central 2'-Deoxy 3'-5' Phosphorothioate oligonuclootide Region For the preparation of a 20 mer oligonucleotide, a first region of 6 RNA nucleotides having 2'-5' linkages is prepared as per the method of Kierzek, et. al., *Nucleic Acids Research* 1992, 20, 1685 on a DNA synthesizer utilizing the general protocols of this reference. Upon completion of the 2'-5' linked region, a 2'-deoxy phosphorothioate region of 3'-5' linked DNA oligonucleotide 8 nucleotides long is added. A further 6 nucleotide long region of 2'-5' linkages is then added to complete the oligonucleotide having mixed 2'-5' and 3'-5' linkages.

EXAMPLE 5

Macromolecule Having Regions Of Cyclobutyl Surrogate Nucloosides Linked By Phosphodiester Linkages Flanking A Central 2'-Deoxy 3'-5' Pbosphorothioate Oligonucleotide Region For the preparation of a 20 mer oligonucleotide, a first region of 6 cyclobutyl surrogate nucleosides linked by phosphodiester linkages is prepared as per Example 38 of U.S. patent application Ser. No. 808,201 (U.S. Pat. No. 5,359,044) on a DNA synthesizer utilizing the protocols of this reference. Upon completion of this region, a 2'-deoxy phosphorothioate region of a 3'-5' linked DNA oligonucleotide 8 nucleotides long is added. A further region of 6 cyclobutyl surrogate nucleosides is then added to complete the macromolecule.

EXAMPLE 6

Macromolecule Having Regions Of Carbocyclic surrogate Nucleosides Linked By Phosphodiester Linkages Flanking A Central 2'-Deoxy Phosphorothioate Oligonucleotide Region Carbocyclic nucleosides are prepare as per the review references cited in Borthwick, et al., *Tetrahedron* 1992, 48, 571. The resulting carbocyclic nucleosides are blocked with a dimethoxytrityl blocking group in the normal manner. The corresponding phosphoramidites are prepared in the manner of Example 38 of U.S. patent application Ser. No. 808,201 substituting the carbocyclic nucleosides for the cyclobutyl nucleosides surrogates. For the preparation of a 18 mer oligonucleotide, a first region of 4 carbocyclic nucleosides linked by phosphodiester linkages is prepared on a DNA synthesizer utilizing the protocols of Example 1. Upon completion of this region, a 2'-deoxy phosphorothioate 3'-5' linked DNA oligonucleotide 8 nucleotides long is added. A further region of 4 carbocyclic nucleotides is added to complete the macromolecule.

EXAMPLE 7

Oligonucleotide Having 4'-Thionucleotide Regions Flanking A Central 2'-Deoxy Phosphorothioate Oligonucleotide Region In the manner of Example 6, a region of 4'-thionucleotides is prepared as per the procedures of PCT patent application PCT/US91/02732. Next a region of normal 2'-deoxy phosphorothioate nucleotides are added followed by a further region of the 4'-thionucleotides.

EXAMPLE 8

Macromolecule Having Peptide Nucleic Acids Regions Flanking A Central 2'-Deoxy Phosphorothioate Oligonucleotide Region A first region of peptide nucleic acids is prepared as per PCT patent application PCT/EP/01219. The peptide nucleic acids are prepared from the C terminus towards the N terminus using monomers having protected amine groups. Following completion of the first peptide region, the terminal amine blocking group is removed and the resulting amine reacted with a 3'-C-(formyl)-2',3'-dideoxy-5'-trityl nucleotide as prepared as per the procedure of Vasseur, et. al., *J. Am. Chem. Soc.* 1992, 114, 4006. The condensation of the amine with the aldehyde moiety of the C-formyl nucleoside is effected as per the conditions of the Vasseur, ibid., to yield an intermediate oxime linkage. The oxime linkage is reduced under reductive alkylation conditions of Vasseur, ibid., with HCHO/NaBH$_3$CN/AcOH to yield the nucleoside connected to the peptide nucleic acid via an methyl alkylated amine linkage. An internal 2'-deoxy phosphorothioate nucleotide region is then continued from this nucleoside as per the protocols of Example 1. Peptide synthesis for the second peptide region is commenced by reaction of the carboxyl end of the first peptide nucleic acid of this second region with the 5' hydroxy of the last nucleotide of the DNA region following removal of the dimethoxytrityl blocking group on that nucleotide. Coupling is effected via DEA in pyridine to form an ester linkage between the peptide and the nucleoside. Peptide synthesis is then continued in the manner of patent application PCT/EP/01219 to complete the second peptide nucleic acid region.

EXAMPLE 9
Oligonucleotide Having 2'-Substituted Oligonucleotide Regions Flanking A Central 2'-Deoxy Phosphoroselenate Oligonucleotide Region An oligonucleotide is prepared as per Example 3 utilizing 2'-O-methyl substituted nucleotides to prepare the flanking regions and oxidization with 3H-1,2-benzothiaseleno-3-ol for introducing the seleno moieties in the central region as per the procedure reported by Stawinski, et al., *Tenth International Roundtable: Nucleosides, Nucleotides and Their Biological Evaluation*, Sep. 16–20, 1992, Abstracts of Papers, Abstract 80.

EXAMPLE 10
Oligonucleotide Having 2'-Substituted Oligonucleotide Regions Flanking A Central 2'-Deoxy Phosphorodithioate Oligonucleotide Region An oligonucleotide is prepared as per Example 3 utilizing 2'-O-aminopropoxy substituted nucleotides to prepare the flanking regions and the procedures of Beaton, et. al., Chapter 5, Synthesis of oligonucleotide phosphorodithioates, page 109, *Oligonucleotides and Analogs, A Practical Approach*, Eckstein, F., Ed.; The Practical Approach Series, IRL Press, New York, 1991 to prepare the internal phosphorodithioate region.

EXAMPLE 11
Oligonucleotide Having Boranophosphate Linked oligonucleotide Regions Flanking A Central 2'-Deoxy Phosphorothioate oligonucleotide Region An oligonucleotide is prepared as per Example 3 utilizing the procedures of published patent application PCT/US/06949 to prepare the flanking boranophosphate regions and the procedures of Example 1 to prepare the central 2'-deoxy phosphorothioate region.

EXAMPLE 12
Oligonucleotide Having 2'-Substituted Methyl Phosphonate Linked Oligonucleotide Regions Flanking A Central 2'-Deoxy Phosphorothioate Oligonucleotide Region 2-Fluoro nucleosides are prepared as per Example 3 and then converted to nucleotides for the preparation of flanking methylphosphonates linkages as per the procedures Miller et. al., Chapter 6, Synthesis of oligo-2'-deoxyribonucleoside methylphosphonates, page 137, *Oligonucleotides and Analogs, A Practical Approach*, Eckstein, F., Ed.; The Practical Approach Series, IRL Press, New York, 1991. The central internal phosphorothioate region is prepared as per Example 1 followed by the addition of a further 2'-O-substituted methylphosphonate region.

EXAMPLE 13
Oligonucleotide Having 2'-Substituted Methyl Phosphotriester Linked Oligonucleotide Regions Flanking Central 2'-Deoxy Phosphodiester Thymidine Oligonucleotide Region 2-Fluoro nucleosides are prepared as per Example 3 and then converted to nucleotides for the preparation of flanking regions of methyl phosphotriester linkages as per the procedures Miller, et. al., *Biochemistry* 1977, 16, 1988. A central internal phosphodiester region having 7 consecutive thymidine nucleotide residues is prepared as per Example 1 followed by the addition of a further 2'-O-substituted methyl phosphotriester region.

EXAMPLE 14
Macromolecule Having Hydroxylamine Oligonucleoside Regions Flanking A Central 2'-Deoxy Phosphorothioate Oligonucleotide Region A first flanking region of nucleosides alternately linked by methylhydroxylamine linkages and phosphodiester linkages is prepared as per the procedure of Vasseur, ibid. A central 2'-O-deoxy phosphorothioate oligonucleotide region is added as per the procedure of Example 3 followed by a further flanking region having the same linkages as the first region to complete the macromolecule.

EXAMPLE 15
Macromolecule Having Hydrazine Linked Oligonucleoside Regions Flanking A Central 2'-Deoxy Phosphorothioate Oligonucleotide Region A first flanking region of nucleosides linked by methylhydrazine linkages is prepared as per the procedures of the examples of patent application PCT/US92/04294. A central 2'-O-deoxy phosphorothioate oligonucleotide region is added as per the procedure of Example 3 followed by a further flanking region having the same linkages as the first region to complete the macromolecule.

EXAMPLE 16
Macromolecule Having Methysulfenyl Linked oligonucleoside Regions Flanking A Central 2'-Deoxy Phosphorothioate Oligonucleotide Region A first flanking region of nucleosides linked by methylsulfenyl linkages is prepared as per the procedures of the examples of patent application PCT/US92/04294. A central 2'-O-deoxy phosphorothioate oligonucleotide region is added as per the procedure of Example 3 followed by a further flanking region having the same linkages as the first region to complete the macromolecule.

EXAMPLE 17
Macromolecule Having Ethanediyliaino Linked Oligonucleoside Regions Flanking A Central 2'-Deoxy Phosphorothioate Oligonucleotide Region A first flanking region of nucleosides linked by 1,2-ethanediylimino linkages is prepared as per the procedures of the examples of patent application PCT/US92/04294. A central 2'-O-deoxy phosphorothioate oligonucleotide region is added as per the procedure of Example 3 followed by a further flanking region having the same linkages as the first region to complete the macromolecule.

EXAMPLE 18
oligonucleotide Having Methylene Phosphonate Linked oligonucleotide Regions Flanking A Central 2'-Deoxy Phosphorothioate Oligonucleotide Region A first flanking region of nucleosides linked by methylene phosphonate linkages is prepared as per the procedure of the examples of patent application PCT/US92/04294. A central 2'-O-deoxy phosphorothioate oligonucleotide region is added as per the procedure of Example 3 followed by a further flanking region having the same linkages as the first region to complete the macromolecule.

EXAMPLE 19
Macromolecule Having Nitrilomethylidyne Linked Oligonucleoside Regions Flanking A Central 2'-Deoxy Phosphorothioate oligonucleotide Region A first flanking region of nucleosides linked by nitrilomethylidyne linkages is prepared as per the procedures of the examples of U.S. patent application Ser No. 903,160. A central 2'-O-deoxy phosphorothioate oligonucleotide region is added as per the procedure of Example 3 followed by a further flanking region having the same linkages as the first region to complete the macromolecule.

EXAMPLE 20
Macromolecule Having Carbonate Linked Oligonucleoside Regions Flanking A Central 2'-Deoxy Phosphorothioate Oligonucleotide Region A first flanking region of nucleosides linked by carbonate linkages is prepared as per the procedure of Mertes, et al., *J. Med. Chem.* 1969, 12, 154. A central 2'-O-deoxy phosphorothioate oligonucleotide region is added as per the procedure of Example 3 followed by a further flanking region having the same linkages as the first region to complete the macromolecule.

EXAMPLE 21
Macromolecule Having Carbamate Linked Oligonucleoside Regions Flanking A Central 2'-Deoxy Phosphorothioate Oligonucleotide Region A first flanking region of nucleosides linked by carbamate linkages is prepared as per the procedure of Gait, et. al., *J. Chem. Soc. Perkin* 1 1974, 1684. A central 2'-O-deoxy phosphorothioate oligonucleotide region is added as per the procedure of Example 3 followed by a further flanking region having the same linkages as the first region to complete the macromolecule.

EXAMPLE 22
Macromolecule Having Silyl Linked Oligonucleoside Regions Flanking A Central 2'-Deoxy Phospborothioate Oligonucleotide Region A first flanking region of nucleosides linked by silyl linkages is prepared as per the procedure of Ogilvie, et al., *Nucleic Acids Res.* 1988, 16, 4583. A central 2'-O-deoxy phosphorothioate oligonucleotide region is added as per the procedure of Example 3 followed by a further flanking region having the same linkages as the first region to complete the macromolecule.

EXAMPLE 23
Macromolecules Having Sulfide, Sulfoxide and Sulfone Linked Oligonucleoside Regions Flanking A Central 2'-Deoxy Phosphorothioate Oligonucleotide Region A first flanking region of nucleosides linked by sulfide, sulfoxide and sulfone linkages is prepared as per the procedure of Schneider, et aI., *Tetrahedron Letters* 1990, 31, 335. A central 2'-O-deoxy phosphorothioate oligonucleotide region is added as per the procedure of Example 3 followed by a further flanking region having the same linkages as the first region to complete the macromolecule.

EXAMPLE 24
Macromolecules Having Sulfonate Linked Oligonucleoside Regions Flanking A Central 2'-Deoxy Phosphorothioate Oligonucleotide Region A first flanking region of nucleosides linked by sulfonate linkages is prepared as per the procedure of Musicki, et al., *J. Org. Chem.* 1991, 55, 4231. A central 2'-O-deoxy phosphorothioate oligonucleotide region is added as per the procedure of Example 3 followed by a further flanking region having the same linkages as the first region to complete the macromolecule.

EXAMPLE 24
Macromolecules Having Sulfonamide Linked Oligonucleoside Regions Flanking A Central 2'-Deoxy Phosphorothioate Oligonucleotide Region A first flanking region of nucleosides linked by sulfonamide linkages is prepared as per the procedure of Kirshenbaum, et. al., *The 5th San Diego Conference: Nucleic Acids: New Frontiers*, Poster abstract 28, Nov. 14–16, 1990. A central 2'-O-deoxy phosphorothioate oligonucleotide region is added as per the procedure of Example 3 followed by a further flanking region having the same linkages as the first region to complete the macromolecule.

EXAMPLE 25
Macromolecules Having Formacetal Linked oligonucleoside Regions Flanking A Central 2'-Deoxy Phospborothioate Oligonucleotide Region A first flanking region of nucleosides linked by formacetal linkages is prepared as per the procedure of Matteucci, *Tetrahedron Letters* 1990, 31, 2385 or Veeneman, et. al., *Recueil des Trav. Chim.* 1990, 109, 449. A central 2'-O-deoxy phosphorothioate oligonucleotide region is added as per the procedure of Example 3 followed by a further flanking region having the same linkages as the first region to complete the macromolecule.

EXAMPLE 26
Macromolecules Having Thioformacetal Linked oligonucleoside Regions Flanking A Central 2'-Deoxy Phosphorothioate Oligonucleotide Region A first flanking region of nucleosides linked by thioformacetal linkages is prepared as per the procedure of Matteucci, et. al., *J. Am. Chem. Soc.* 1991, 113, 7767 or Matteucci, *Nucleosides & Nucleotides* 1991, 10, 231. A central 2'-O-deoxy phosphorothioate oligonucleotide region is added as per the procedure of Example 3 followed by a further flanking region having the same linkages as the first region to complete the macromolecule.

EXAMPLE 27
Macromolecules Having Morpholine Linked Oligonucleoside Regions Flanking A Central 2'-Deoxy Phosphorothioate Oligonucleotide Region A first flanking region of nucleosides linked by morpholine linkages is prepared as per the procedure of U.S. Pat. No. 5,034,506. A central 2'-O-deoxy phosphorothioate oligonucleotide region is added as per the procedure of Example 3 followed by a further flanking region having the same linkages as the first region to complete the macromolecule.

EXAMPLE 28
Macromolecules Having Amide Linked oligonucleoside Regions Flanking A Central 2'-Deoxy Phosphorothioate Oligonucleotide Region A first flanking region of nucleosides linked by amide linkages is prepared as per the procedure of U.S. patent application Ser. No. 703,619 filed May 21, 1991 (U.S. Pat. No. 5,378,825) and related PCT patent application PCT/US92/04305. A central 2'-O-deoxy phosphorothioate oligonucleotide region is added as per the procedure of Example 3 followed by a further flanking region having the same linkages as the first region to complete the macromolecule.

EXAMPLE 29
Macromolecules Having Ethylene Oxide Linked Oligonucleoside Regions Flanking A Central 2'-Deoxy Phosphodiester Oligonucleotide Region A first flanking region of nucleosides linked by ethylene oxide linkages is prepared as per the procedure of PCT patent application PCT/US91/05713. A central 2'-O-deoxy phosphodiester oligonucleotide region three nucleotides long is added as per the procedure of Example 1 followed by a further flanking region having the same linkages as the first region to complete the macromolecule.

EXAMPLE 30
Macromolecules Having 3,4-Dihydroxybutyl Linked Nucleobase Regions Flanking A Central 2'-Deoxy Phosphorothioate Oligonucleotide Region A first flanking region of nucleobases linked by 3,4-dihydroxybutyl linkages is prepared as per the procedure of Augustyns, et. al., *Nucleic Acids Research* 1991, 19, 2587. A central 2'-O-deoxy phosphorothioate oligonucleotide region is added as per the procedure of Example 3 followed by a further flanking region having the same linkages as the first region to complete the macromolecule.

EXAMPLE 31
Macromolecules Having Dihydroxypropoxymethyl Linked Nucleobase Regions Flanking A Central 2'-Deoxy Phosphorothioate oligonucleotide Region A first flanking region of nucleobases linked by dihydroxypropoxymethyl linkages is prepared as per the procedure of Schneider, et al., *J. Am. Chem. Soc.* 1990, 112, 453. A central 2'-O-deoxy phosphorothioate oligonucleotide region 9 nucleotides long is added as per the procedure of Example 3 followed by a further flanking region having the same linkages as the first region to complete the macromolecule.

PROCEDURE 1
Ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. H-ras gene templates were purchased from the American Type Culture Collection (ATCC numbers 41000 and 41001) in Bethesda, Md. The oligonucleotide PCR primers 5'-ACA-TTA-TGC-TAG-CTT-TTT-GAG-TAA-ACT-TGT-GGG-GCA-GGA-GAC-CCT-GT-3' (sense), SEQ ID NO: 7, and 5'-GAG-ATC-TGA-AGC-TTC-TGG-ATG-GTC-AGC-GC-3' (antisense), SEQ ID NO: 8, were used in standard PCR reactions using mutant and non-mutant H-ras genes as templates. These primers are expected to produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were 5'-GAG-ATC-TGA-AGC-TTG-AAG-ACG-CCA-AAA-CA-TAA-AG-3' (sense), SEQ ID NO: 9, and 5'-ACG-CAT-CTG-GCG-CGC-CGA-TAC-CGT-CGA-CCT-CGA-3' (antisense), SEQ ID NO: 10, were used in standard PCR reactions using a commercially available plasmid (pT3/T7-Luc) (Clontech), containing the luciferase reporter gene, as a template. These primers were expected to yield a product of approximately 1.9 kb corresponding to the luciferase gene, flanked by HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter.

PROCEDURE 2
Transfection of Cells with Plasmid DNA:

Transfections were performed as described by Greenberg, M. E. in Current Protocols in Molecular Biology, (Ausubel, et al., eds.), John Wiley and Sons, NY, with the following modifications. HeLa cells were plated on 60 mm dishes at 5×10⁵ cells/dish. A total of 10 $\mu$g of DNA was added to each dish, of which 9 $\mu$g was ras-luciferase reporter plasmid and 1 $\mu$g was a vector expressing the rat glucocorticoid receptor under control of the constitutive ROUS sarcoma virus (RSV) promoter. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pre-treated with antisense oligonucleotides prior to activation of reporter gene expression by dexamethasone.

PROCEDURE 3
oliqonucleotide Treatment of Cells

Immediately following plasmid transfection, cells were washed three times with Opti-MEM (Gibco), prewarmed to 37° C. Two ml of Opti-MEM containing 10 $\mu$g/ml N-[1-(2,3-dioleyloxy) propyl]—N,N,N,-trimethylammonium chloride (DOTMA) (Bethesda Research Labs, Gaithersburg, Md.) was added to each dish and oligonucleotides were added directly and incubated for 4 hours at 37° C. Opti-MEM was then removed and replaced with the appropriate cell growth medium containing oligonucleotide. At this time, reporter gene expression was activated by treatment of cells with dexamethasone to a final concentration of 0.2 μM. Cells were harvested 12–16 hours following steroid treatment.

PROCEDURE 4
Luciferase Assays

Luciferase was extracted from cells by lysis with the detergent Triton X-100, as described by Greenberg, M. E., in Current Protocols in Molecular Biology, (Ausubel, et al., eds.), John Wiley and Sons, NY. A Dynatech ML1000 luminometer was used to measure peak luminescence upon addition of luciferin (Sigma) to 625 μM. For each extract, luciferase assays were performed multiple times, using differing amounts of extract to ensure that the data were gathered in the linear range of the assay.

PROCEDURE 5
Antisense oligonucleotide Inhibition of ras-Luciferase Gene Expression A series of antisense phosphorothioate oligonucleotide analogs targeted to the codon-12 point mutation of activated H-ras were tested using the ras-luciferase reporter gene system described in the foregoing examples. This series comprised a basic sequence and analogs of that basic sequence. The basic sequence was of known activity as reported in patent application Ser. No. 07/715,196 identified above. In both the basic sequence and its analogs, each of the nucleotide subunits incorporated phosphorothioate linkages to provide nuclease resistance. Each of the analogs incorporated nucleotide subunits that contained 2'-O-methyl substitutions and 2'-deoxy-erythro-pentofuranosyl sugars. In the analogs, a sub-sequence of the 2'-deoxy-erythro-pentofuranosyl sugar containing subunits were flanked on both ends by sub-sequences of 2'-O-methyl substituted subunits. The analogs differed from one another with respect to the length of the sub-sequence of the 2'-deoxy-erythro-pentofuranosyl sugar containing nucleotides. The length of these sub-sequences varied by 2 nucleotides between 1 and 9 total nucleotides. The 2'-deoxy-erythro-pentofuranosyl nucleotide sub-sequences were centered at the point mutation of the codon-12 point mutation of the activated ras.

The base sequences, sequence reference numbers and sequence ID numbers of these oligonucleotides (all are phosphorothioate analogs) are shown in Table 1. In this table those nucleotides identified with a "$^M$" contain a 2'-O-methyl substituent group and the remainder of the nucleotides identified with a "$^d$" are 2'-deoxy-erythro-pentofuranosyl nucleotides.

TABLE 1

| Oligo ref. no. | Sequence | SEQ ID NO: |
|---|---|---|
| 2570 | $C_d C_d A_d\ C_d A_d C_d\ C_d G_d A_d\ C_d G_d G_d\ C_d G_d C_d\ C_d C_d$ | 1 |
| 3975 | $C^M C^M A^M\ C^M A^M C^M\ C^M G^M A_d\ C^M G^M G^M\ C^M G^M C^M\ C^M C^M$ | 2 |
| 3979 | $C^M C^M A^M\ C^M A^M C^M\ C^M G_d A_d\ C_d G^M G^M\ C^M G^M C^M\ C^M C^M$ | 3 |
| 3980 | $C^M C^M A^M\ C^M A^M C^M\ C_d G_d A_d\ C_d G_d G^M\ C^M G^M C^M\ C^M C^M$ | 4 |

TABLE 1-continued

| Oligo ref. no. | Sequence | SEQ ID NO: |
|---|---|---|
| 3985 | $C^M C^M A^M\ C^M A^M C_d\ C_d G_d A_d\ C_d G_d G_d\ C^M G^M C^M\ C^M C^M$ | 5 |
| 3984 | $C^M C^M A^M\ C^M A_d C_d\ C_d G_d A_d\ C_d G_d G_d\ C_d G^M C^M\ C^M C^M$ | 6 |

FIG. 1 shows dose-response data in which cells were treated with the phosphorothioate oligonucleotides of Table 1. Oligonucleotide 2570 is targeted to the codon-12 point mutation of mutant (activated) H-ras RNA. The other nucleotides have 2'-O-methyl substituents groups thereon to increase binding affinity with sections of various lengths of inter-spaced 2'-deoxy-erythro-pentofuranosyl nucleotides. The control oligonucleotide is a random phosphorothioate oligonucleotide analog, 20 bases long. Results are expressed as percentage of luciferase activity in transfected cells not treated with oligonucleotide. As the figure shows, treatment of cells with increasing concentrations of oligonucleotide 2570 resulted in a dose-dependent inhibition of ras-luciferase activity in cells expressing the mutant form of ras-luciferase. Oligonucleotide 2570 displays an approximate threefold selectivity toward the mutant form of ras-luciferase as compared to the normal form.

As is further seen in FIG. 1, each of the oligonucleotides 3980, 3985 and 3984 exhibited greater inhibition of ras-luciferase activity than did oligonucleotide 2570. The greatest inhibition was displayed by oligonucleotide 3985 that has a sub-sequence of 2'-deoxy-erythro-pentofuranosyl nucleotides seven nucleotides long. Oligonucleotide 3980, having a five nucleotide long 2'-deoxy-erythro-pentofuranosyl nucleotide sub-sequence exhibited the next greatest inhibition followed by oligonucleotide 3984 that has a nine nucleotide 2'-deoxy-erythro-pentofuranosyl nucleotide sub-sequence.

Figure 2:
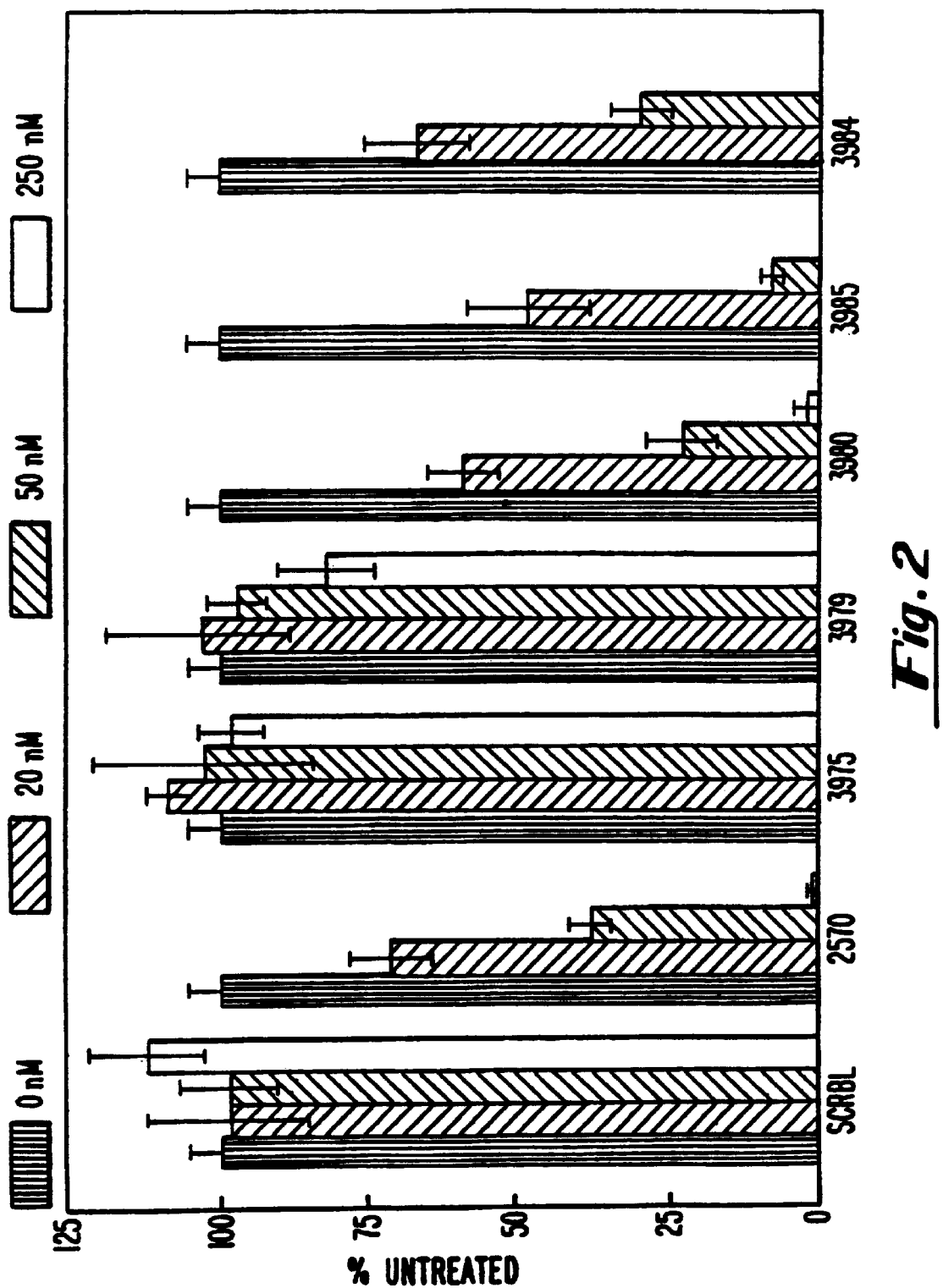
FIG. 2 is a bar chart showing dose response activity of oligonucleotides of the invention and reference compounds..

FIG. 2 shows the results similar to FIG. 1 except it is in bar graph form. Further seen on FIG. 2 is the activity of oligonucleotide 3975 and oligonucleotide 3979. These oligonucleotides have sub-sequences of 2'-deoxy-erythro-pentofuranosyl nucleotides one and three nucleotides long, respectively. As is evident from FIG. 2 neither of the oligonucleotides having either the one nor the three 2'-deoxy-erythro-pentofuranosyl nucleotide sub-sequences showed significant activity. There was measurable activity for the three nucleotide sub-sequence oligonucleotide 3979 at the highest concentration dose.

The increases in activity of oligonucleotides 3980, 3985 and 3984 compared to oligonucleotide 2570 is attributed to the increase in binding affinity imparted to these compounds by the 2'-O-methyl substituent groups located on the compounds and by the RNase H activation imparted to these compounds by incorporation of a sub-sequence of 2'-deoxy-erythro-pentofuranosyl nucleotides within the main sequence of nucleotides. In contrast to the active compounds of the invention, it is interesting to note that sequences identical to those of the active oligonucleotides 2570, 3980, 3985 and 3984 but having phosphodiester linkages in stead of the phosphorothioate linkages of the active oligonucleotides of the invention showed no activity. This is attributed to these phosphodiester compounds being substrates for nucleases that degrade such phosphodiester compounds thus preventing them potentially activating RNase H.

What is claimed is:

1. A method of modifying in vitro a sequence-specific ribonucleic acid, comprising contacting a test solution containing RNase HI and said sequence-specific ribonucleic acid with an oligonucleotide having a sequence of nucleotides under conditions that effect hybridization of said sequence-specific ribonucleic acid and said oligonucleotide, where at least one of said nucleotides is functionalized to increase nuclease resistance of the oligonucleotide, where a plurality of the nucleotides have a substituent group located thereon to increase binding affinity of the oligonucleotide to a complementary strand of sequence-specific ribonucleic acid, and where a plurality of the nucleotides have 2'-deoxy-erythro-pentofuranosyl sugar moieties.

2. The method of claim 1 wherein said substituent group for increasing binding affinity comprises a 2'-substituent group.

3. The method of claim 1 wherein said substituent group for increasing binding affinity comprises a 2'-substituent group that is fluoro, C1–C9 alkoxy, C1–C9 aminoalkoxy, allyloxy, imidazolealkoxy or poly(ethylene glycol).

4. The method of claim 1 wherein each of said nucleotides is a phosphorothioate or phosphorodithioate nucleotide.

5. The method of claim 1 wherein the 3' terminal nucleotide of said oligonucleotide includes a nuclease resistance modifying group on at least one of the 2' or the 3' positions of said nucleotide.

6. The method of claim 1 wherein:
a plurality of said nucleotides bear substituent groups that increases binding affinity of said oligonucleotide to said sequence-specific ribonucleic acid, said substituent-bearing nucleotides being divided into a first nucleotide unit sub-sequence and a second nucleotide unit sub-sequence; and
said plurality of 2'-deoxy-erythro-pentofuranosyl nucleotides is positioned in said sequence of nucleotides between said first nucleotide unit sub-sequence and said second nucleotide unit sub-sequence.

7. The method of claim 1 wherein:
a plurality of said nucleotides bear substituent groups that increase binding affinity of said oligonucleotide to said complementary strand of nucleic acid; and
at least a portion of said substituent-bearing nucleotides are consecutively located at one of the 3' terminus or the 5' terminus of said oligonucleotide.

8. The method of claim 1 wherein at least five of said nucleotides have 2'-deoxy-erythro-pentofuran-osyl sugar moieties, said at least five 2'-deoxy-erythro-pentofuranosyl nucleotides being consecutively located in said sequence of nucleotides.

9. The method of claim 1 wherein from one to about eight of said nucleotides bear a substituent group that increases the binding affinity of said oligonucleotide to said complementary strand, said substituent-bearing nucleotides being consecutively located in said sequence of nucleotides.

10. The method of claim 1 wherein:
from one to about eight of said nucleotides bear a substituent group for increasing the binding affinity of said oligonucleotide to said complementary strand, said substituent-bearing nucleotides being consecutively located in said sequence of nucleotides; and
at least five of said nucleotides have 2'-deoxy-erythro-pentofuranosyl sugar moieties, said at least five 2'-deoxy-erythro-pentofuranosyl nucleotides being consecutively located in said sequence of nucleotides.

11. A method of modifying in vitro a sequence-specific ribonucleic acid, comprising contacting a test solution containing a RNase H and said sequence-specific ribonucleic acid with a compound comprising a plurality of units linked by covalent linkages in a sequence, wherein said contacting occurs under conditions that effect hybridization of said sequence-specific ribonucleic acid and said compound, and:
said units are selected from nucleosides and nucleobases:
said nucleosides are selected from α-nucleosides, β-nucleosides including 2'-deoxy-erythro-pentofuranosyl β-nucleosides, 4'-thionucleosides, and carbocyclic-nucleosides;
said nucleobases are selected from purin-9-yl and pyrimidin-1-yl heterocyclic bases;
said linkages are selected from charged 3'–5' phosphorous, neutral 3'–5' phosphorous, charged 2'–5' phosphorous, neutral 2'–5' phosphorous or non-phosphorous linkages; and
said sequence of linked units is divided into at least two regions, wherein:
a first of said regions includes said nucleobases linked by non-phosphorous linkages and nucleobases that are attached to phosphate linkages via non-sugar tethering groups, and nucleosides selected from said α-nucleosides linked by charged and neutral 3'–5' phosphorous linkages, said α-nucleosides linked by charged and neutral 2'–5' phosphorous linkages, said α-nucleosides linked by non-phosphorous linkages, said 4'-thionucleosides linked by charged and neutral 3'–5' phosphorous linkages, said 4'-thionucleosides linked by charged and neutral 2'–5' phosphorous linkages, said 4'-thionucleosides linked by non-phosphorous linkages, said carbocyclic-nucleosides linked by charged and neutral 3'–5' phosphorous linkages, said carbocyclic-nucleosides linked by charged and neutral 2'–5' phosphorous linkages, said carbocyclic-nucleosides linked by non-phosphorous linkages, said β-nucleosides linked by charged and neutral 2'–5' linkages, and said β-nucleosides linked by non-phosphorous linkages; and
a second of said regions includes said 2'-deoxy-erythro-pentofuranosyl β-nucleosides linked by charged 3'–5' phosphorous linkages having a negative charge at physiological pH.

12. The method of claim 11 wherein said first region includes at least two nucleobases linked by a non-phosphate linkage.

13. The method of claim 12 wherein said non-phosphate linkage is a peptide linkage.

14. The method of claim 11 wherein said second region is positioned between said first region and a third region, said third region including said nucleobases linked by non-phosphorous linkages and nucleobases that are attached to phosphate linkages via a non-sugar tethering moiety, and nucleosides selected from said α-nucleosides linked by charged and neutral 3'–5' phosphorous linkages, said α-nucleosides linked by charged and neutral 2'–5' phosphorous linkages, said α-nucleosides linked by non-phosphorous linkages, said 4'-thionucleosides linked by charged and neutral 3'–5' phosphorous linkages, said 4'-thionucleosides linked by charged and neutral 2'–5' phosphorous linkages, said 4'-thionucleosides linked by non-phosphorous linkages, said carbocyclic-nucleosides linked by charged and neutral 3'–5' phosphorous linkages, said carbocyclic-nucleosides linked by charged and neutral 2'–5' phosphorous linkages, said carbocyclic-nucleosides linked by non-phosphorous linkages, said β-nucleosides linked by charged and neutral 2'–5' linkages, and said β-nucleosides linked by non-phosphorous linkages.

15. A method of claim 11 wherein said nucleobases are selected from adenine, guanine, cytosine, uracil, thymine, xanthine, hypoxanthine, 2-aminoadenine, 6-methyl and other alkyl adenine, 2-propyl and other alkyl adenine, 5-halo uracil and cytosine, 6-azo uracil, cytosine and thymine, 5-uracil (pseudouracil), 4-thiouracil, 8-halo, amino, thiol, thiolalkyl, hydroxyl and other 8 substituted adenine and guanine, or 5-trifluoromethyl uracil and cytosine.

* * * * *